United States Patent
Ono et al.

(10) Patent No.: US 7,126,141 B2
(45) Date of Patent: Oct. 24, 2006

(54) ELECTROOPTIC SYSTEM ARRAY, CHARGED-PARTICLE BEAM EXPOSURE APPARATUS USING THE SAME, AND DEVICE MANUFACTURING METHOD

(75) Inventors: Haruhito Ono, Kanagawa (JP); Masato Muraki, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/168,425

(22) Filed: Jun. 29, 2005

(65) Prior Publication Data

US 2005/0253082 A1    Nov. 17, 2005

Related U.S. Application Data

(62) Division of application No. 09/819,737, filed on Mar. 29, 2001, now Pat. No. 6,965,153.

(30) Foreign Application Priority Data

| Mar. 31, 2000 | (JP) | ............... 2000-097069 |
| Aug. 1, 2000 | (JP) | ............... 2000-233145 |

(51) Int. Cl.
 G21K 5/00  (2006.01)
(52) U.S. Cl. .............. 250/492.23; 250/492.21; 250/492.2; 250/492.3
(58) Field of Classification Search ........... 250/492.23
See application file for complete search history.

(56) References Cited

U.S. PATENT DOCUMENTS

| 3,755,704 A | 8/1973 | Spindt et al. ............... 313/309 |
| 4,200,794 A | 4/1980 | Newberry et al. ... 250/396 ML |
| 4,354,111 A | 10/1982 | Williams et al. ......... 250/396 R |
| 4,419,182 A | 12/1983 | Westerberg et al. ........ 156/644 |
| 4,419,580 A | 12/1983 | Walker et al. .......... 250/396 R |
| 4,569,033 A | 2/1986 | Collins et al. .............. 364/845 |
| 4,607,167 A | 8/1986 | Petric ....................... 250/492.2 |
| 4,742,234 A | 5/1988 | Feldman et al. ......... 250/492.2 |
| 5,105,089 A | 4/1992 | Yamada ................... 250/492.2 |

(Continued)

FOREIGN PATENT DOCUMENTS

JP    56-19402    5/1981

(Continued)

OTHER PUBLICATIONS

"Sub-Nanometer Miniature Electron Microscope", A.D. Feinerman, et al., Journal of Vacuum Science and Technology A, vol. 10, No. 4, Jul./Aug. 1992, 611-616.

(Continued)

Primary Examiner—John R. Lee
Assistant Examiner—James J. Leybourne
(74) Attorney, Agent, or Firm—Fitzpatrick, Cella, Harper & Scinto

(57) ABSTRACT

A charged-particle beam exposure apparatus includes a charged-particle beam source for emitting a charged-particle beam, an electrooptic system array which has a plurality of electron lenses and forms a plurality of intermediate images of the charged-particle beam source by the plurality of electron lenses, and a projection electrooptic system for projecting on a substrate the plurality of intermediate images formed by the electrooptic system array. The electrooptic system array includes at least two electrodes arranged along paths of a plurality of charged-particle beams, each of the at least two electrodes having a plurality of apertures on the paths of the plurality of charged-particle beams, and a shield electrode which is interposed between the at least two electrodes and has a plurality of shields corresponding to the respective paths of the plurality of charged-particle beams.

4 Claims, 19 Drawing Sheets

U.S. PATENT DOCUMENTS

| | | | | |
|---|---|---|---|---|
| 5,121,234 A * | 6/1992 | Kucera | | 349/69 |
| 5,215,623 A | 6/1993 | Takahashi et al. | | 156/644 |
| 5,260,579 A | 11/1993 | Yasuda et al. | | 250/492.2 |
| 5,324,930 A | 6/1994 | Jech, Jr. | | 257/435 |
| 5,534,311 A | 7/1996 | Shaw et al. | | 427/526 |
| 5,604,394 A | 2/1997 | Saito et al. | | 313/422 |
| 5,617,131 A | 4/1997 | Murano et al. | | 347/233 |
| 5,637,907 A * | 6/1997 | Leedy | | 257/434 |
| 5,726,539 A | 3/1998 | Spanjer et al. | | 315/382 |
| 5,731,591 A | 3/1998 | Yamada | | 250/492.2 |
| 5,834,783 A | 11/1998 | Muraki et al. | | 250/398 |
| 5,838,119 A | 11/1998 | Engle | | 315/366 |
| 5,864,142 A | 1/1999 | Muraki et al. | | 250/491.1 |
| 5,905,267 A | 5/1999 | Muraki | | 250/492.22 |
| 5,929,454 A | 7/1999 | Muraki et al. | | 250/491.1 |
| 5,939,725 A | 8/1999 | Muraki | | 250/492.22 |
| 5,942,761 A | 8/1999 | Tuli | | 250/556 |
| 5,973,332 A | 10/1999 | Muraki et al. | | 250/492.2 |
| 5,981,954 A | 11/1999 | Muraki | | 250/397 |
| 6,013,976 A | 1/2000 | Gorski et al. | | 313/412 |
| 6,014,200 A | 1/2000 | Sogard et al. | | 355/533 |
| 6,072,251 A | 6/2000 | Markle | | 310/12 |
| 6,104,035 A | 8/2000 | Muraki | | 250/492.22 |
| 6,107,636 A | 8/2000 | Muraki | | 250/492.2 |
| 6,121,625 A | 9/2000 | Ito et al. | | 250/492.22 |
| 6,137,103 A | 10/2000 | Giles et al. | | 250/216 |
| 6,137,113 A | 10/2000 | Muraki | | 250/492.2 |
| 6,166,387 A | 12/2000 | Muraki et al. | | 250/492.2 |
| 6,184,850 B1 | 2/2001 | Suzuki et al. | | 345/74 |
| 6,188,074 B1 | 2/2001 | Satoh et al. | | 250/492.22 |
| 6,274,877 B1 | 8/2001 | Muraki | | 250/492.23 |
| 6,323,499 B1 | 11/2001 | Muraki et al. | | 250/492.22 |
| 6,337,485 B1 | 1/2002 | Muraki | | 250/492.2 |
| 6,381,072 B1 * | 4/2002 | Burger | | 359/622 |
| 6,465,796 B1 | 10/2002 | Haraguchi et al. | | 250/492.23 |
| 6,469,799 B1 | 10/2002 | Kajita | | 358/1.16 |
| 6,472,672 B1 | 10/2002 | Muraki | | 250/492.2 |
| 6,483,120 B1 | 11/2002 | Yui et al. | | 250/491.1 |
| 6,515,409 B1 | 2/2003 | Muraki et al. | | 313/359.1 |
| 6,566,664 B1 | 5/2003 | Muraki | | 250/492.2 |
| 6,603,128 B1 | 8/2003 | Maehara et al. | | 250/441.11 |
| 6,617,595 B1 | 9/2003 | Okunuki | | 250/492.22 |
| 6,657,210 B1 | 12/2003 | Muraki | | 250/492.22 |
| 6,777,697 B1 | 8/2004 | Yui et al. | | 250/492.22 |
| 6,872,950 B1 | 3/2005 | Shimada et al. | | 250/396 R |
| 6,872,951 B1 | 3/2005 | Yagi et al. | | 250/396 R |
| 6,872,952 B1 | 3/2005 | Shimada et al. | | 250/396 R |
| 6,903,345 B1 | 6/2005 | Ono et al. | | 250/396 R |
| 6,903,352 B1 | 6/2005 | Muraki et al. | | 250/492.22 |
| 2001/0052576 A1 * | 12/2001 | Shimada et al. | | 250/492.1 |
| 2001/0054690 A1 * | 12/2001 | Shimada et al. | | 250/306 |
| 2002/0009901 A1 | 1/2002 | Maehara et al. | | 438/795 |
| 2002/0051111 A1 * | 5/2002 | Greene et al. | | 349/149 |
| 2002/0063531 A1 * | 5/2002 | Aarnink | | 315/169.3 |
| 2002/0160311 A1 | 10/2002 | Muraki et al. | | 430/296 |
| 2002/0179855 A1 | 12/2002 | Muraki | | 250/492.22 |
| 2003/0094584 A1 | 5/2003 | Yui et al. | | 250/492.22 |
| 2003/0209673 A1 | 11/2003 | Ono et al. | | 250/396 R |
| 2004/0061064 A1 | 4/2004 | Ono et al. | | 250/396 R |

FOREIGN PATENT DOCUMENTS

| | | |
|---|---|---|
| JP | 6-44093 | 2/1994 |
| JP | 2001-126651 | 5/2001 |

OTHER PUBLICATIONS

"High Aspect Ratio Aligned Multilayer Microstructure Fabrication", K. Y. Lee, et al., Journal of Vacuum Science and Technology B, vol. 12, No. 6, Nov./Dec. 1994, pp. 3425-3430.

"Arrayed Miniature Electron Beam Columns For High Throughput Sub-100 nm Lithography", T. H. P. Chang, et al., Journal of Vacuum Science and Technology B, vol. 10, No. 6, Nov./Dec. 1992, pp. 2743-2748.

"Microstructures for Particle Beam Control", G. W. Jones, et al., Journal of Vacuum Science and Technology B, vol. 6, No. 6, Nov./Dec. 1988, pp. 2023-2027.

"A Multibeam Scheme for Electron-Beam Lithography", T. Sasaki, Journal of Vacuum Science and Technology, vol. 19, No. 4, Nov./Dec. 1981, pp. 963-965.

* cited by examiner

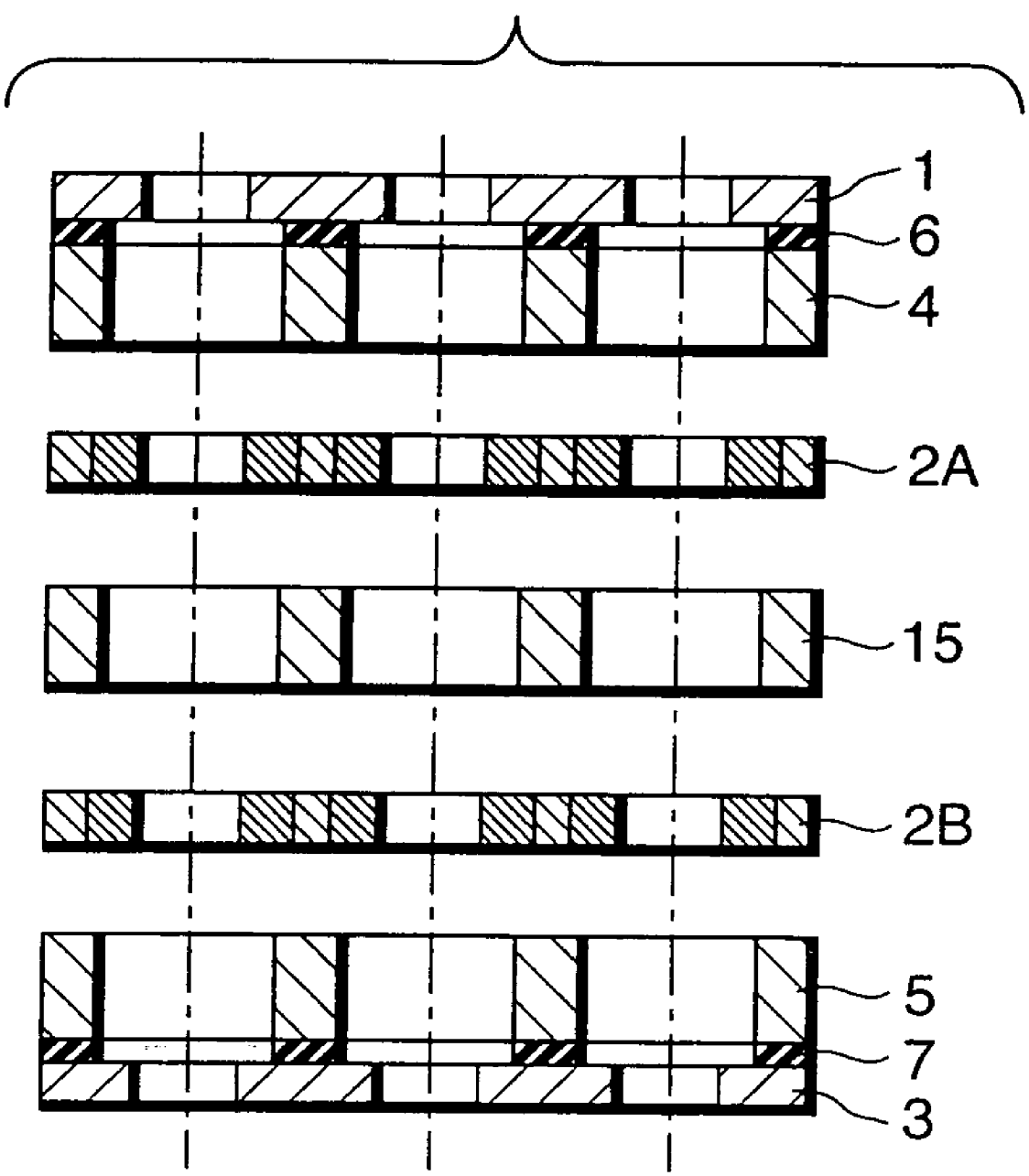

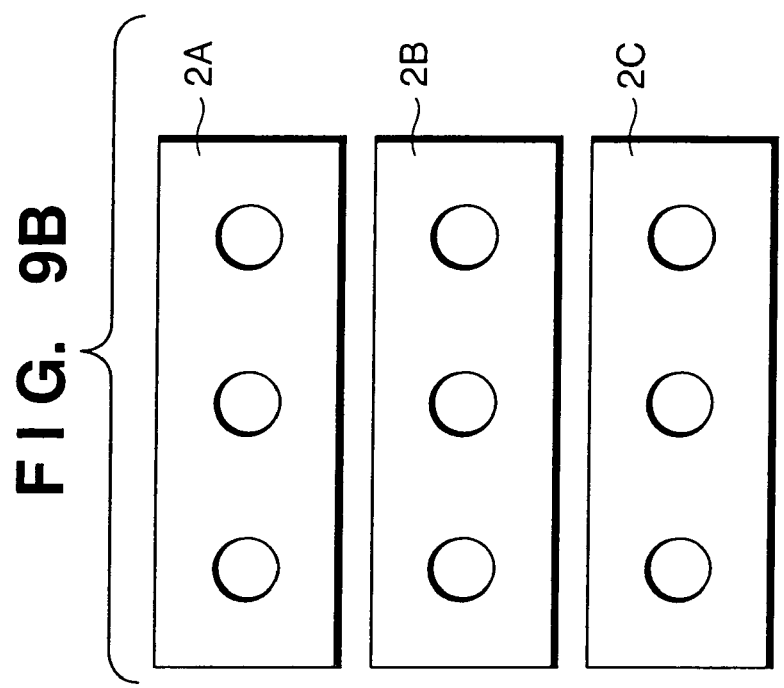
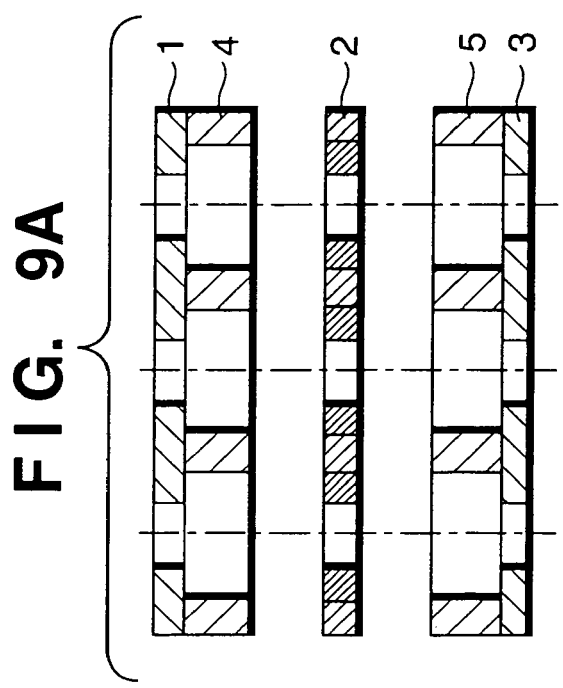
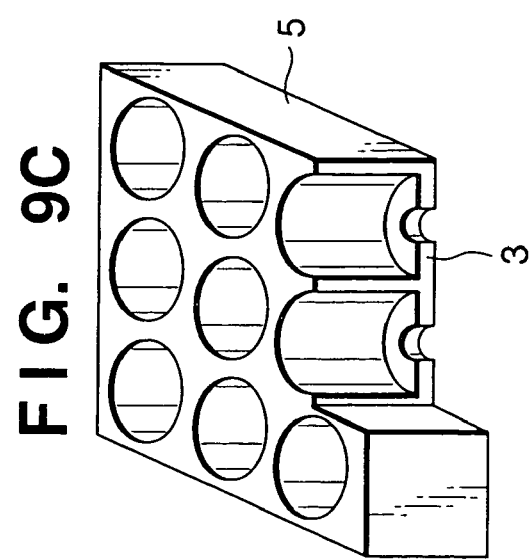

FIG. 17

```
URL  http://www.maintain.co.jp/db/input.html

TROUBLE DB INPUT WINDOW

OCCURRENCE DATE  [2000/3/15] ~4040
TYPE OF APPARATUS [**********] ~4010
SUBJECT          [OPERATION ERROR (START-UP ERROR)] ~4030
SERIAL NUMBER S/N [465NS4580001] ~4020
DEGREE OF URGENCY [D] ~4050
SYMPTOM   LED IS KEPT FLICKERING AFTER
          POWER-ON                              ~4060

REMEDY    POWER ON AGAIN
          (PRESS RED BUTTON IN ACTIVATION)      ~4070

PROGRESS  INTERIM HAS BEEN DONE                 ~4080

(SEND) (RESET)        4100              4110              4120
LINK TO RESULT LIST DATABASE   SOFTWARE LIBRARY   OPERATING GUIDE
```

ELECTROOPTIC SYSTEM ARRAY, CHARGED-PARTICLE BEAM EXPOSURE APPARATUS USING THE SAME, AND DEVICE MANUFACTURING METHOD

This application is a divisional application of U.S. patent application Ser. No. 09/819,737, filed Mar. 29, 2001 now U.S. Pat. No. 6,965,153.

FIELD OF THE INVENTION

The present invention pertains to the technical field of an electrooptic system suitable for an exposure apparatus using charged-particle beams such as electron beams, and relates to an electrooptic system array having an array of a plurality of electrooptic systems.

BACKGROUND OF THE INVENTION

In the production of semiconductor devices, an electron beam exposure technique receives a great deal of attention as a promising candidate of lithography capable of micropattern exposure at a line width of 0.1 μm or less. There are several electron beam exposure methods. An example is a variable rectangular beam method of drawing a pattern with one stroke. This method suffers many problems as a mass-production exposure apparatus because of low throughput. To attain a high throughput, there is proposed a pattern projection method of reducing and transferring a pattern formed on a stencil mask. This method is advantageous with respect to a simple repetitive pattern, but disadvantageous with respect to a random pattern, such as a logic interconnection pattern, in terms of the throughput, and a low productivity disables practical application.

To the contrary, a multi-beam system for drawing a pattern simultaneously with a plurality of electron beams without using any mask has been proposed and is very advantageous for practical use because of the absence of physical mask formation and exchange. What is important in using multi-electron beams is the number of electron lens arrays used in this system. The number of electron lenses formed in an array determines the number of beams, and is a main factor which determines the throughput. Downsizing the electron lenses while improving the performance of them is one of the keys to improve the performance of the multi-beam exposure apparatus.

Electron lenses are classified into electromagnetic and electrostatic types. The electrostatic electron lens does not require any coil core or the like, is simpler in structure than the electromagnetic electron lens, and is more advantageous to downsizing. Principal prior art concerning downsizing of the electrostatic electron lens (electrostatic lens) will be described.

A. D. Feinerman et al. (J. Vac. Sci. Technol. A10(4), page 611, 1992) disclose a three-dimensional structure made up of three electrodes as a single electrostatic lens by a micromechanical technique using a V-groove formed by a fiber and Si crystal anisotropic etching. The Si film has a membrane frame, membrane and an aperture formed in the membrane, so as to transmit an electron beam. K. Y. Lee et al. (J. Vac. Sci. Technol. B12(6), page 3, 425, 1994) disclose a multilayered structure of Si and Pyrex glass fabricated by using anodic bonding. This technique fabricates microcolumn electron lenses aligned at a high precision. Sasaki (J. Vac. Sci. Technol. 19, page 693, 1981) discloses an Einzel lens made up of three electrodes having lens aperture arrays. Chang et al. (J. Vac. Sci. Technol. B10, page 2,743, 1992) disclose an array of microcolumns having Einzel lenses.

In the prior art, if many aperture electrodes are arrayed, and different lens actions are applied to electron beams, the orbit and aberration change under the influence of the surrounding electrostatic lens field, and so-called crosstalk occurs in which electron beams are difficult to operate independently.

Crosstalk will be explained in detail with reference to FIG. 10. Three types of electrodes, i.e., an upper electrode 1, middle electrodes 2, and a lower electrode 3 constitute an Einzel lens. The upper and lower electrodes 1 and 3 are 10 μm in thickness and have 80-μm diameter apertures arrayed at a pitch of 200 μm. The middle electrodes 2 are 50 μm in thickness, have a cylindrical shape of 80 μm in inner diameter, and are arrayed at a pitch of 200 μm. The distances between the upper and middle electrodes 1 and 2 and between the middle and lower electrodes 2 and 3 are 100 μm. The upper and lower electrodes 1 and 3 receive a potential of 0 [V], middle electrodes 2 on central and upper rows B and A receive −1,000 [V], and middle electrodes 2 on a lower row C receive −950 [V]. The potential difference between adjacent electrodes is 50 [V]. When an electron beam having a beam diameter of 40 μm and an energy of 50 keV enters a central aperture from the left of the upper electrode 1, a downward shift angle Δθ of the electron beam becomes several tens of μ rad or more. A typical allowable value of the shift angle Δθ is 1 μ rad or less. In this electrode arrangement, the shift angle exceeds the allowable range. That is, the electron beam is influenced by the surrounding lens field, and so-called crosstalk occurs, which must be solved.

SUMMARY OF THE INVENTION

The present invention has been made to overcome the conventional drawbacks, and has as its principal object to provide an improvement of the prior art. It is an object of the present invention to provide an electrooptic system array which realizes various conditions such as downsizing, high precision, and high reliability at a high level. It is another object of the present invention to provide an electrooptic system array improved by reducing crosstalk unique to a multi-beam. It is still another object of the present invention to provide a high-precision exposure apparatus using the electrooptic system array, a high-productivity device manufacturing method, a semiconductor device production factory, and the like.

According to the first aspect of the present invention, there is provided an electrooptic system array having a plurality of electron lenses, comprising at least two electrodes arranged along paths of a plurality of charged-particle beams, each of at least two electrodes having a plurality of apertures on the paths of the plurality of charged-particle beams, and a shield electrode, which is interposed between at least two electrodes and has a plurality of shields corresponding to the respective paths of the plurality of charged-particle beams.

According to a preferred mode of the present invention, each shield has an aperture on a path of a corresponding charged-particle beam, and/or the shield electrode is constituted by integrating the plurality of shields. According to another preferred mode of the present invention, the shield electrode may be insulated from at least two electrodes or may be integrated with one of at least two electrodes. According to still another preferred mode of the present invention, the plurality of shields of the shield electrode receive the same potential, and/or receive a potential different from a potential applied to at least two electrodes. According to still another preferred mode of the present invention, the aperture of each shield of the shield electrode is larger in size than the apertures of at least two electrodes. According to still another preferred mode of the present invention, at least two electrodes include first and second electrodes, each of the first and second electrodes has a plurality of electrode elements with apertures on the paths of the plurality of charged-particle beams, the plurality of electrode elements of the first electrode are grouped in units of rows in a first direction, electrode elements which belong to each group being connected, and the plurality of electrode elements of the second electrode are grouped in units of rows in a second direction different from the first direction, electrode elements which belong to each group being connected.

According to the second aspect of the present invention, there is provided an electrooptic system array having a plurality of electron lenses, comprising upper, middle, and lower electrodes arranged along paths of a plurality of charged-particle beams, the upper, middle, and lower electrodes having pluralities of apertures on the paths of the plurality of charged-particle beams, an upper shield electrode which is interposed between the upper and middle electrodes and has a plurality of shields corresponding to the respective paths of the plurality of charged-particle beams, and a lower shield electrode which is interposed between the lower and middle electrodes and has a plurality of shields corresponding to the respective paths of the plurality of charged-particle beams.

According to a preferred mode of the present invention, the middle electrode includes a plurality of electrode elements having apertures on the paths of the plurality of charged-particle beams. According to another preferred mode of the present invention, the electrooptic system array preferably further comprises a middle shield electrode between the plurality of electrode elements of the middle electrode. According to still another preferred mode of the present invention, it is preferable that the plurality of electrode elements of the middle electrode be grouped in units of, e.g., rows, and electrode elements which belong to each group be electrically connected to each other. Alternatively, it is preferable that the middle electrode have a plurality of rectangular electrode units electrically separated in units of rows, and each electrode unit have a plurality of apertures on the paths of corresponding charged-particle beams.

According to still another preferred mode of the present invention, the respective shields of the upper and lower shield electrodes preferably have apertures on the paths of the charged-particle beams. According to still another preferred mode of the present invention, it is preferable that the upper shield electrode be constituted by integrating the plurality of shields, and the lower shield electrode be constituted by integrating the plurality of shields. According to still another preferred mode of the present invention, it may be possible that the upper shield electrode is insulated from the upper and middle electrodes, and the lower shield electrode is insulated from the lower and middle electrodes, or that the upper shield electrode is integrated with the upper electrode, and the lower shield electrode is integrated with the lower electrode. According to still another prefer-red mode of the present invention, the plurality of shields of the upper shield electrode and the plurality of shields of the lower shield electrode receive the same potential, and/or receive a potential different from a potential applied to the upper and lower electrodes. According to still another preferred mode of the present invention, an aperture of each shield of the upper shield electrode and an aperture of each shield of the lower shield electrode are larger in size than an aperture of the middle electrode. According to still another preferred mode of the present invention, an interval between the middle electrode and the upper shield electrode and an interval between the middle electrode and the lower shield electrode are smaller than a pitch of a plurality of apertures of the middle electrode.

According to the third aspect of the present invention, there is provided a charged-particle beam exposure apparatus comprising a charged-particle beam source for emitting a charged-particle beam, an electrooptic system array which has a plurality of electron lenses and forms a plurality of intermediate images of the charged-particle beam source by the plurality of electron lenses, and a projection electrooptic system for projecting on a substrate the plurality of intermediate images formed by the electrooptic system array, the electrooptic system array including at least two electrodes arranged along paths of a plurality of charged-particle beams, each of at least two electrodes having a plurality of apertures on the paths of the plurality of charged-particle beams, and a shield electrode which is interposed between at least two electrodes and has a plurality of shields corresponding to the respective paths of the plurality of charged-particle beams.

According to the fourth aspect of the present invention, there is provided a charged-particle beam exposure apparatus comprising a charged-particle beam source for emitting a charged-particle beam, an electrooptic system array which has a plurality of electron lenses and forms a plurality of intermediate images of the charged-particle beam source by the plurality of electron lenses, and a projection electrooptic system for projecting on a substrate the plurality of intermediate images formed by the electrooptic system array, the electrooptic system array including upper, middle, and lower electrodes arranged along paths of a plurality of charged-particle beams, the upper, middle, and lower electrodes having pluralities of apertures on the paths of the plurality of charged-particle beams, an upper shield electrode which is interposed between the upper and middle electrodes and has a plurality of shields corresponding to the respective paths of the plurality of charged-particle beams, and a lower shield electrode which is interposed between the lower and middle electrodes and has a plurality of shields corresponding to the respective paths of the plurality of charged-particle beams.

According to the fifth aspect of the present invention, there is provided a device manufacturing method comprising the steps of installing a plurality of semiconductor manufacturing apparatuses including the charged-particle beam exposure apparatus in a factory, and manufacturing a semiconductor device by using the plurality of semiconductor manufacturing apparatuses. In this case, this manufacturing method preferably further comprises the steps of connecting the plurality of semiconductor manufacturing apparatuses by a local area network, connecting the local area network to an external network of the factory, acquiring information about the charged-particle beam exposure apparatus from a database on the external network by using the local area network and the external network, and controlling the charged-particle beam exposure apparatus on the basis of the acquired information.

According to the sixth aspect of the present invention, there is provided a semiconductor manufacturing factory comprising a plurality of semiconductor manufacturing apparatuses, including the charged-particle beam exposure apparatus, a local area network for connecting the plurality of semiconductor manufacturing apparatuses, and a gateway for connecting the local area network to an external network of the semiconductor manufacturing factory.

According to the seventh aspect of the present invention, there is provided a maintenance method for a charged-particle beam exposure apparatus, comprising the steps of preparing a database for storing information about maintenance of the charged-particle beam exposure apparatus on an external network of a factory where the charged-particle beam exposure apparatus is installed, connecting the charged-particle beam exposure apparatus to a local area network in the factory, and maintaining the charged-particle beam exposure apparatus on the basis of the information stored in the database by using the external network and the local area network.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 6 is a sectional view for explaining another structure of an electrooptic system array;

FIGS. 9A to 9C are views for explaining still another structure of an electrooptic system array;

FIG. 17 is a view showing a user interface on a display;

DETAILED DESCRIPTION OF THE PREFERRED EMBODIMENTS

<Electrooptic System Array>

Figure 1C:
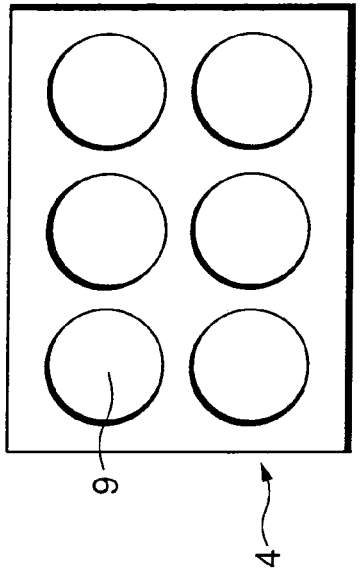
FIGS. 1A to 1D are views for explaining the structure of an electrooptic system array.
Figure 1D:
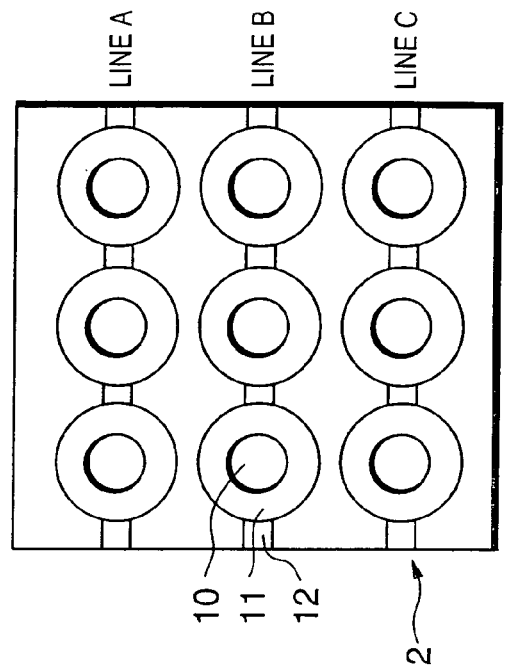
Figure 1A:
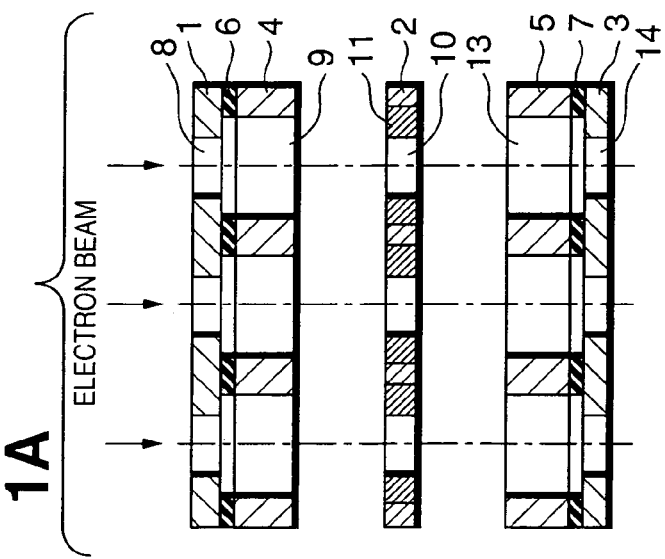
Figure 1B:
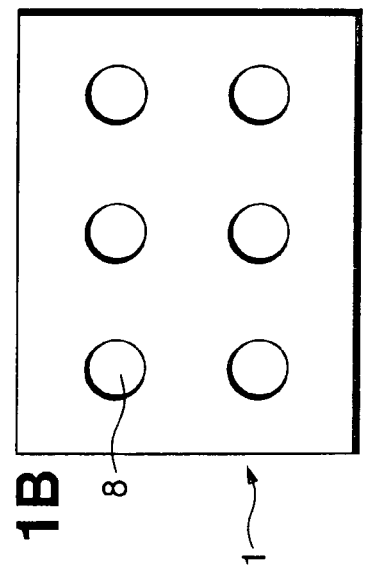

An electrooptic system array according to an embodiment of the present invention will be described. FIG. 1A is an exploded sectional view of the electrooptic system array. The electrooptic system array shown in FIG. 1A is constituted by sequentially stacking, on the paths of a plurality of electron beams (charged-particle beams), an upper electrode 1, upper shield electrode 4, middle electrode 2, lower shield electrode 5, and lower electrode 3, each of which has a plurality of apertures. FIG. 1B is a plan view of the upper electrode 1 when viewed from the top, FIG. 1C is a plan view of the upper shield electrode 4 when viewed from the top, and FIG. 1D is a plan view of the middle electrode 2 when viewed from the top.

The upper electrode 1 has a thin-film structure 10 μm in thickness that is formed from an electrode layer of a conductive material (e.g., Cu or Au), and has a plurality of 80-μm diameter circular apertures 8 arrayed regularly at a pitch of 200 μm. The lower electrode 3 also has the same structure, and has a plurality of apertures 14 at positions corresponding to the apertures of the upper electrode. The middle electrode 2 comprises cylindrical electrode elements (apertured electrode elements) 11 of a conductive material (e.g., Cu or Au) (thickness: 50 μm, inner diameter: 80 μm, outer diameter: 170 μm) having apertures 10. The cylindrical electrode elements 11 are grouped in units of rows (rows A, B, and C), and cylindrical electrode elements 11 included in each row are electrically connected by a wiring line 12 of Cu, Au, or the like with a width of 4 μm. The upper and lower shield electrodes 4 and 5 respectively have circular apertures 9 and 13 with an inner diameter of 160 μm that are formed in an 88-μm thick conductive (e.g., Cu or Au) plate regularly at a pitch of 200 μm. The sizes (inner diameter sizes) of the apertures of the upper and lower shield electrodes 4 and 5 are larger than those of the middle, upper, and lower electrodes 2, 1, and 3. This reduces the influence of inserting the shield electrode on the lens action.

The apertures regularly arrayed in the upper electrode 1, upper shield electrode 4, middle electrode 2, shield electrode 5, lower electrode 3, and middle electrode 2 are formed on the paths of electron beams such that the centers of the apertures coincide with each other when viewed along the optical axis. The upper electrode 1 and upper shield electrode 4 are joined via an insulating layer 6, whereas the lower electrode 3 and lower shield electrode 5 are joined via an insulating layer 7. The insulating layers 6 and 7 are 1 μm in thickness, so that the distances between the upper electrode 1 and the upper shield electrode 4 and between the lower electrode 3 and the lower shield electrode 5 are 1 μm. The distances between the upper and middle electrodes 1 and 2 and between the lower and middle electrodes 3 and 2 are 100 μm. The upper shield electrode 4 is insulated from the middle electrode 2, while the lower shield electrode 5 is insulated from the middle electrode 2.

Figure 10:
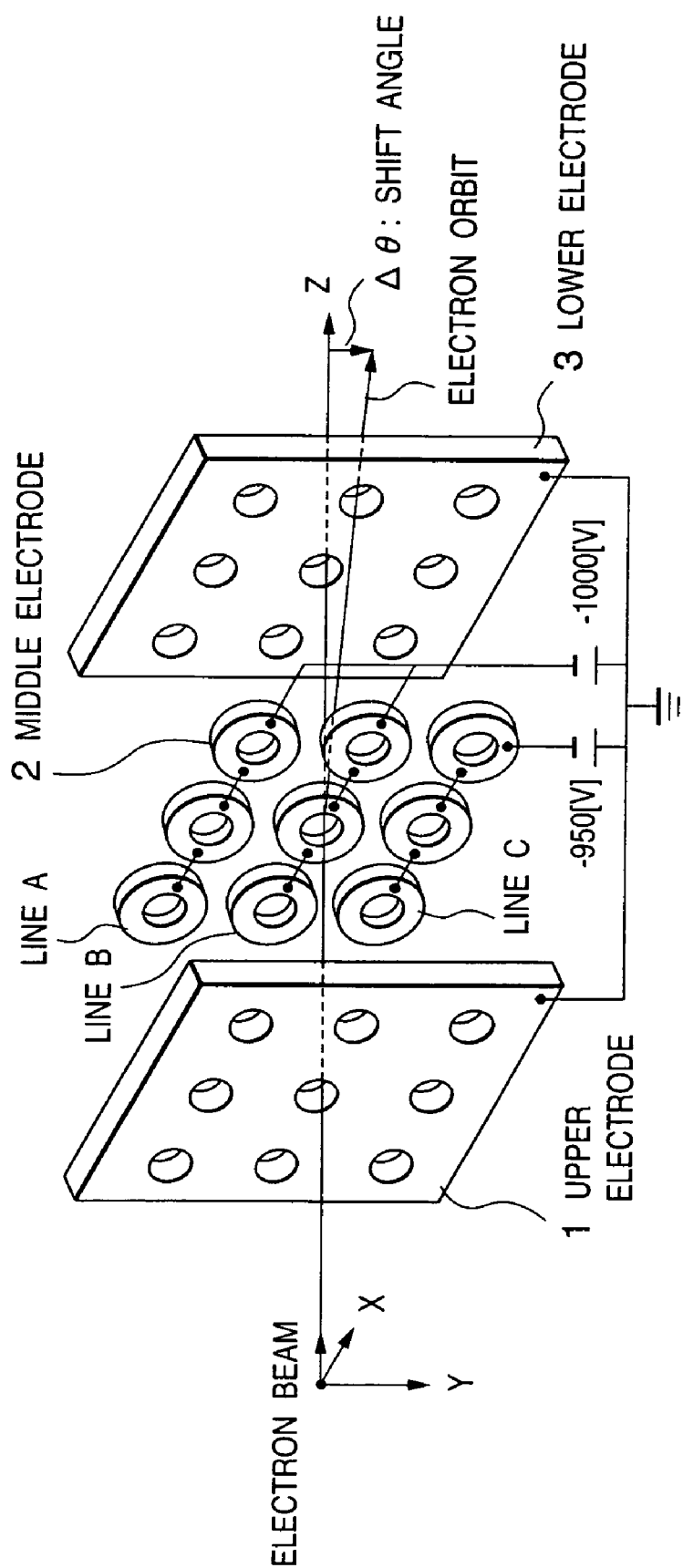
FIG. 10 is a view for explaining generation of crosstalk.

In the electrooptic system array having this arrangement, similar to FIG. 10, the upper electrode 1, upper shield electrode 4, lower shield electrode 5, and lower electrode 3 receive a potential of 0 [V], row B (central row) and row A of the middle electrode 2 receive a potential of –1,000 [V], and row C of the middle electrode 2 receives a potential of –950 [V]. The adjacent potential difference between rows B and C is 50 [V]. At this time, the beam shift angle Δθ is 0.8 mμ rad, and the beam diameter (least circle of confusion) is 0.6 μm, which fall within their allowable ranges and are suppressed to a negligible degree in practical use.

According to this embodiment, the shield electrodes 4 and 5 are respectively interposed between the upper and middle electrodes 1 and 2 and between the middle and lower electrodes 2 and 3 in correspondence with a plurality of apertures in the electrooptic system array having the upper, middle, and lower electrodes 1, 2 and 3, which have pluralities of apertures and are stacked along the electron beam path. This structure can suppress the influence of an adjacent lens field and can satisfactorily suppress crosstalk.

A method of fabricating an electrooptic system array having the above structure will be explained. For descriptive convenience, only one aperture will be exemplified.

A method of fabricating a structure made up of the upper electrode 1 and upper shield electrode 4 will be described with reference to FIGS. 2A to 2F. A structure made up of the lower electrode 3 and lower shield electrode 5 can also be formed by the same method.

Figure 2A:
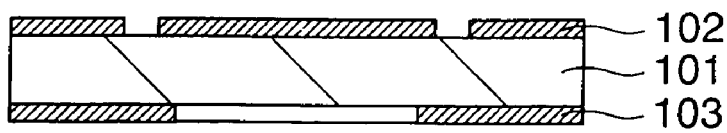
FIGS. 2A to 2F are sectional views for explaining a method of fabricating an upper electrode (lower electrode) and shield electrode.

A silicon wafer 101 of the <100> direction is prepared as a substrate, and 300-nm thick silicon nitride films are formed on the respective surfaces of the silicon wafer 101 by CVD (Chemical Vapor Deposition). By resist and etching processes, patterned silicon nitride films 102 and 103 are formed as a result of removing the silicon nitride films at a portion serving as a prospective optical path of an electron beam and a portion used to align electrodes (FIG. 2A).

Figure 2B:
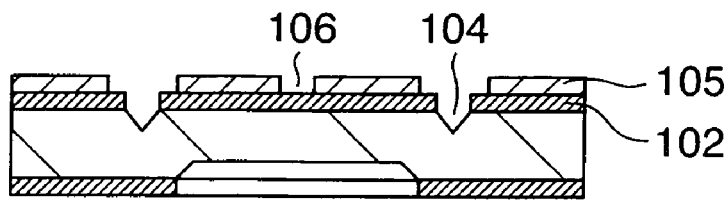

The silicon substrate 101 is anisotropically etched to a depth of 1 to 2 μm with an aqueous tetramethylammonium hydroxide solution using the silicon nitride films 102 and 103 as a mask, thus forming V-grooves 104 in at least one surface of the substrate. Chromium and gold films are successively deposited to film thicknesses of 50 nm and 1 μm as an upper electrode 105 (corresponding to 1 in FIG. 1A) on the surface having the V-grooves 104. A resist pattern is formed on these films, and the gold and chromium films are etched using the resist pattern as a mask, thereby forming an electron beam aperture 106 (FIG. 2B).

Figure 2C:
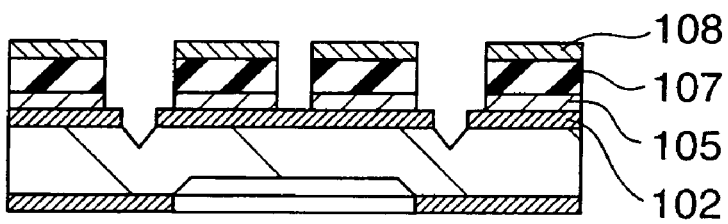

An SiO$_2$ film (insulating film) 107 is sputtered to 1 μm and patterned. Chromium and gold films are successively deposited to film thicknesses of 5 nm and 50 nm as a plating electrode film 108 for forming an upper shield electrode 110 (corresponding to 4 in FIG. 1A), and patterned (FIG. 2C).

Figure 2D:
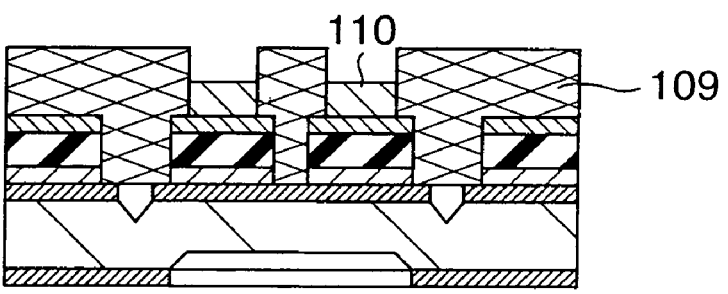

A resist pattern 109 serving as a plating mold is formed on the plating electrode 108. More specifically, the resist is made of SU-8 (MicroChem. Co) mainly consisting of an epoxidized bisphenol A oligomer, and is formed to a film thickness of 110 μm. Exposure employs a contact type exposure apparatus using a high-pressure mercury lamp. After exposure, post-exposure bake (PEB) is done on a hot plate at 85° C. for 30 min. After the substrate is gradually cooled to room temperature, the resist is developed with propylene glycol monomethyl ether acetate for 5 min to complete the plating mold pattern 109. An 89-μm thick gold pattern 110 serving as an upper shield electrode (corresponding to 4 in FIG. 1A) is buried in the apertures of the resist pattern 109 by electroplating (FIG. 2D).

Figure 2E:
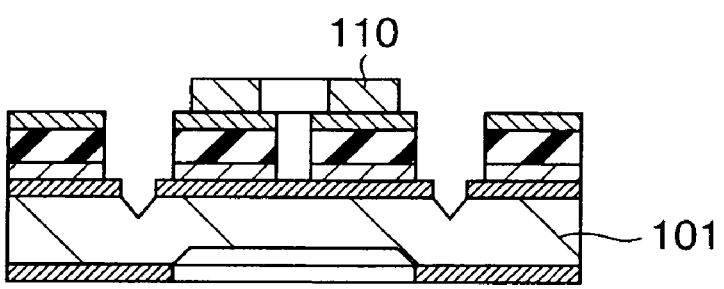

The SU-8 resist 109 is removed, and the substrate is cleaned and dried by IPA (FIG. 2E).

Figure 2F:
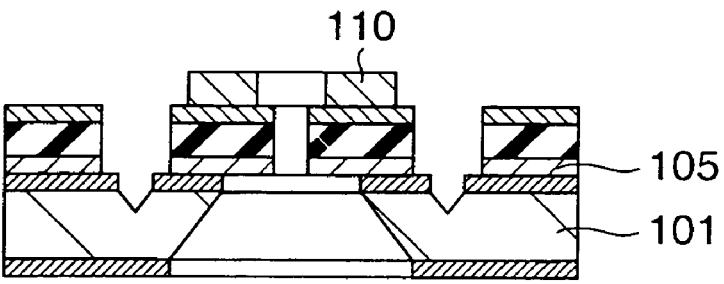

The plating surface is protected with polyimide (not shown). The silicon substrate 101 is etched back from the other surface at 90° C. with a 22% aqueous tetramethylammonium hydroxide solution. Etching is continued until silicon is etched away and the silicon nitride film 102 is exposed. The substrate is cleaned with water and dried. The silicon nitride film 102 exposed after etching of silicon is etched away by using tetrafluoromethane in a dry etching apparatus. The polyimide film which protects the other surface is removed by ashing (FIG. 2F).

Figure 3A:
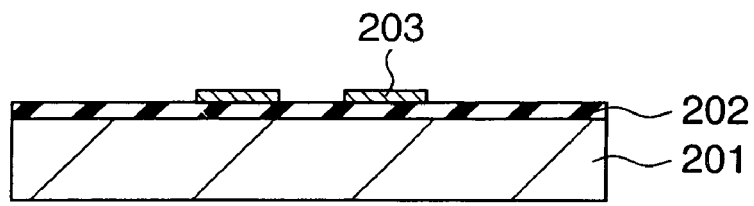
FIGS. 3A to 3D are sectional views for explaining a method of fabricating a middle electrode.

The middle electrode 2 is fabricated as follows. A silicon wafer is prepared as a substrate 201, and an SiO$_2$ film 202 is formed to a thickness of 50 nm by sputtering. A plating electrode film 203 for fabricating a middle electrode 205 (corresponding to 2 in FIG. 1A) is formed by depositing gold to a film thickness of 50 nm and patterning it (FIG. 3A).

Figure 3B:
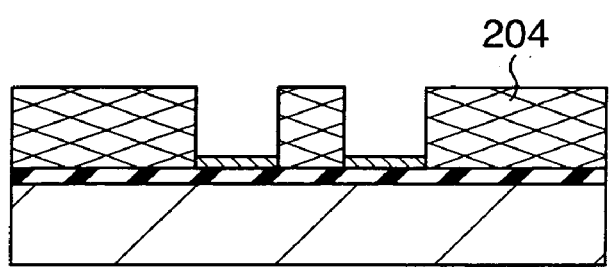

A resist pattern 204 serving as a plating mold is formed. More specifically, the resist is made of SU-8 (MicroChem. Co) mainly consisting of an epoxidized bisphenol A oligomer, and is formed to a film thickness of 80 μm. Exposure employs a contact type exposure apparatus using a high-pressure mercury lamp. After exposure, post-exposure bake (PEB) is done on a hot plate at 85° C. for 30 min. After the substrate is gradually cooled to room temperature, the resist is developed with propylene glycol monomethyl ether acetate for 5 min to complete the plating mold pattern 204 (FIG. 3B).

Figure 3C:
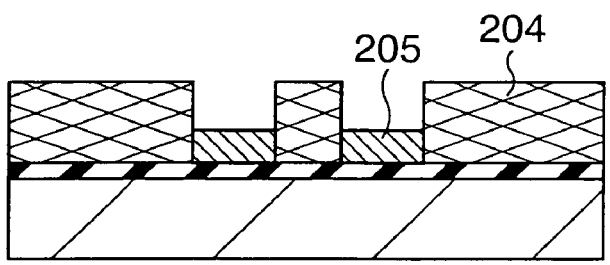

A 50-μm thick gold pattern 205 is buried as the middle electrode (corresponding to 2 in FIG. 1A) in the apertures of the resist pattern 204 by electroplating (FIG. 3C).

Figure 3D:
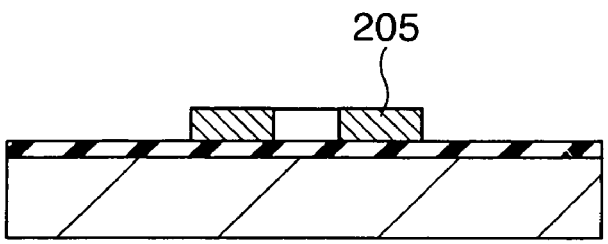

The SU-8 resist 204 is removed in N-methyl-pyrrolidone (NMP), and the substrate is cleaned and dried by IPA (FIG. 3D).

A method of joining the middle electrode and a structure made up of a lower electrode and lower shield electrode will be explained with reference to FIGS. 4A to 4D. As described above, the structure made up of the lower electrode and lower shield electrode is fabricated by the same method as the method of fabricating the structure made up of the upper electrode and upper shield electrode.

Figure 4A:
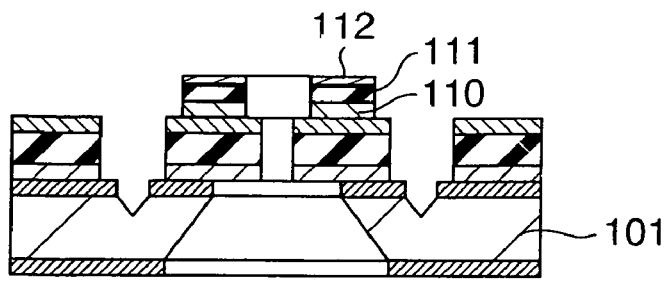
FIGS. 4A to 4D are sectional views for explaining a method of joining electrodes.
Figure 4B:
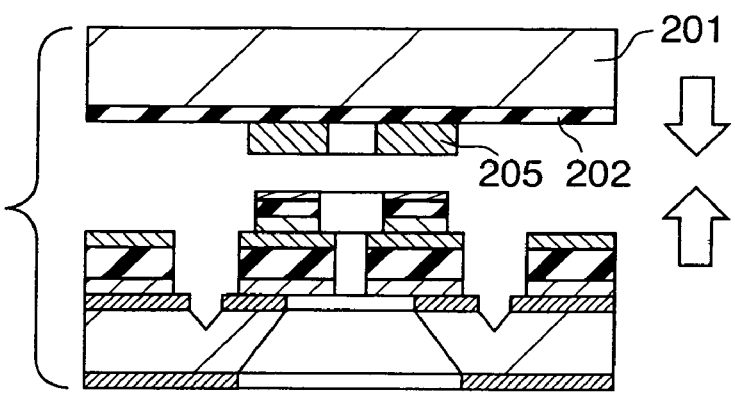
Figure 4C:
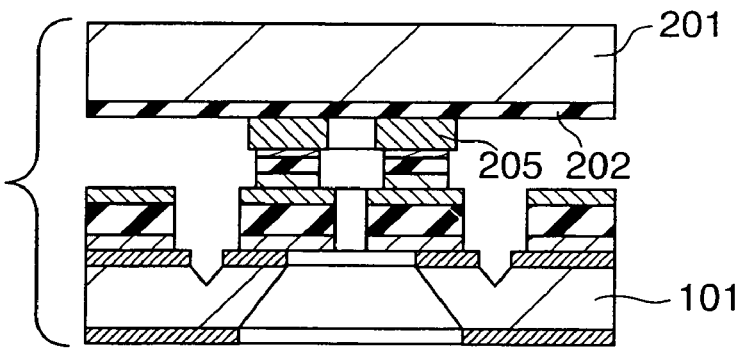
Figure 4D:
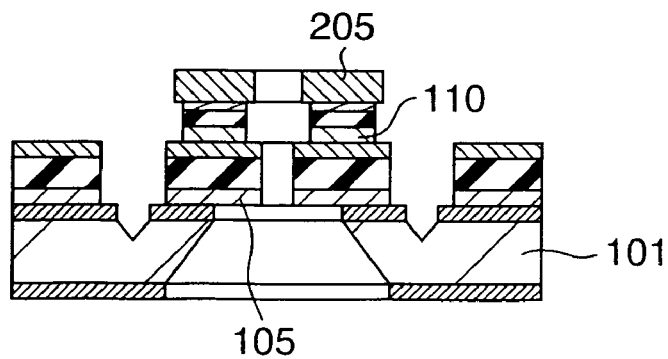

A lower electrode and lower shield electrode shown in FIG. 2F that are fabricated by the procedures of FIGS. 2A to 2F are prepared. After an SiO$_2$ film (insulating film) 111 is formed to 10 μm by sputtering and patterned, a gold film 112 is deposited to 50 nm and patterned (FIG. 4A). The middle electrode prepared by the procedures shown in FIGS. 3A to 3D is turned over and pressed against the gold film 112 by gold-to-gold contact bonding (FIGS. 4B and 4C). Only the silicon wafer of the middle electrode is wet-etched with a jig. The gold and SiO$_2$ films are sequentially dry-etched away by 50 nm each to obtain a lower electrode/middle electrode structure (FIG. 4D).

Figure 5:
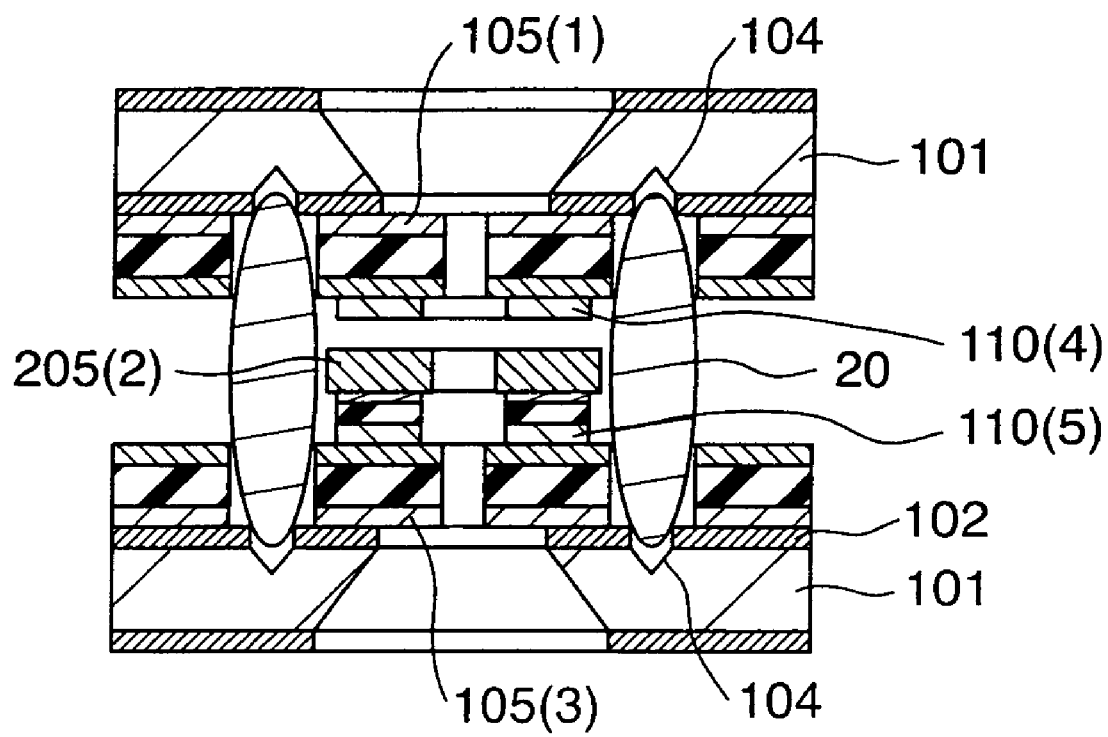
FIG. 5 is a sectional view for explaining a state in which the electrodes are completely joined.

FIG. 5 is a view for explaining the final assembly. The structure shown in FIG. 4D that is fabricated by the procedures shown in FIGS. 4A to 4D and constituted by the joined lower electrode 105 (corresponding to 3 in FIG. 1A), lower shield electrode 110 (corresponding to 5 in FIG. 1A), and middle electrode 205 (corresponding to 11 in FIG. 1A) faces the structure shown in FIG. 2F that is fabricated by the procedures shown in FIGS. 2A to 2F and constituted by the upper electrode 105 (corresponding to 1 in FIG. 1A) and upper shield electrode 110 (corresponding to 4 in FIG. 1A). Fibers 20 are set in the alignment V-grooves 104 formed on the two sides of the substrate. The two structures are pressed to achieve alignment in directions parallel and perpendicular to the joined surface. The aligned members are fixed with an adhesive. Accordingly, an electrooptic element array with high assembly precision is completed.

Several modifications of the above-described electrooptic system array will be explained. FIG. 6 is an exploded view showing an arrangement having a plurality of middle electrodes. Compared to the embodiment of FIG. 1A using one middle electrode, the electrooptic system array of FIG. 6 has two middle electrodes 2A and 2B which sandwich a middle shield electrode 15.

Figure 7B:
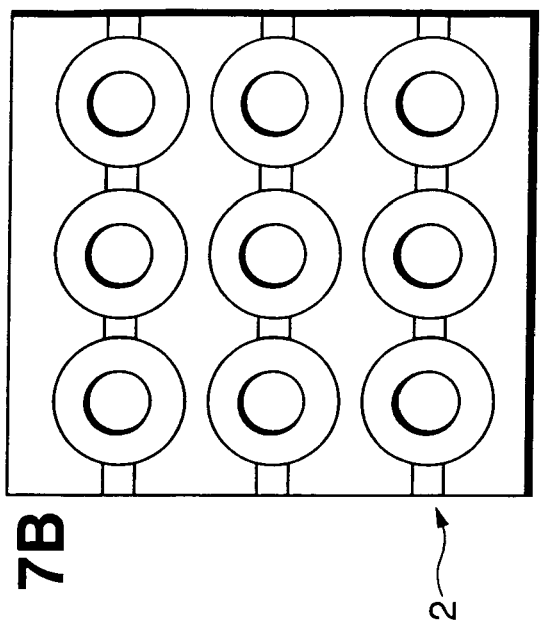
FIGS. 7A to 7C are views for explaining still another structure of an electrooptic system array.
Figure 7C:
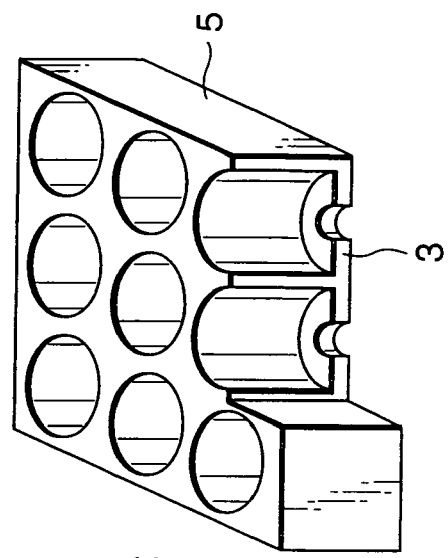
Figure 7A:
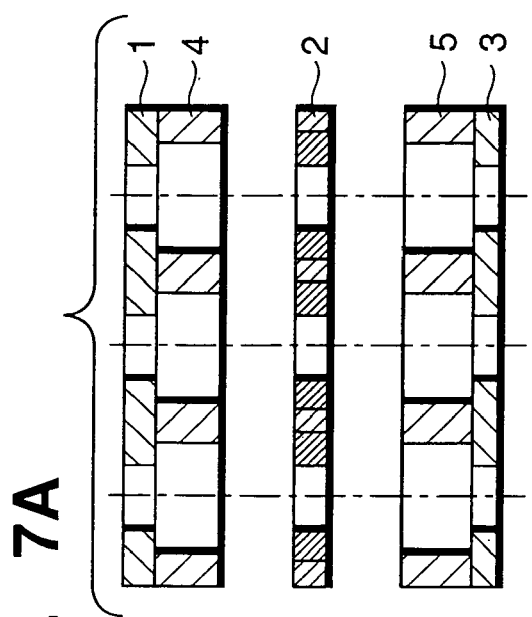

FIGS. 7A to 7C show another embodiment of an electrooptic system array in which a shield electrode is not separate, but is integrated into one electrode. FIG. 7A is an exploded sectional view of the electrooptic system array, FIG. 7B is a plan view of a middle electrode 2 when viewed from the top, and FIG. 7C is a perspective view of a lower electrode 3, lower shield 5, upper electrode 1, and upper shield 4. In this electrooptic system array, the upper electrode 1 and upper shield electrode 4 and the lower electrode 3 and lower shield electrode 5 are integrated structures of a metal material, respectively, and no insulating layer is interposed in each electrode and a corresponding shield electrode. This can simplify the manufacturing process.

Figure 8A:
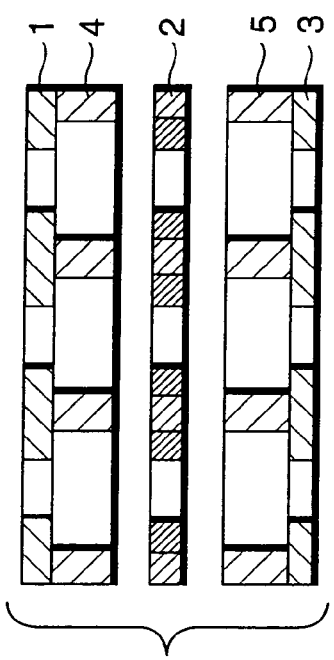
FIGS. 8A to 8D are views for explaining still another structure of an electrooptic system array.
Figure 8D:
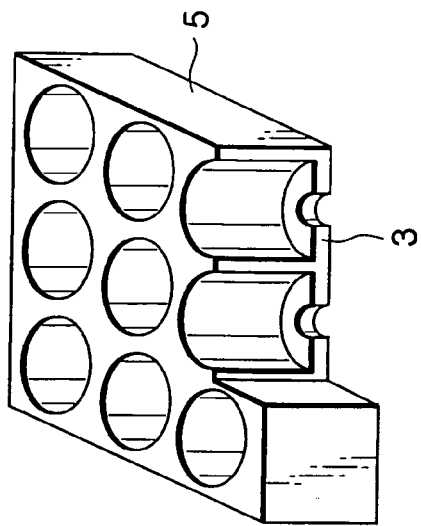
Figure 8C:
Figure 8B:
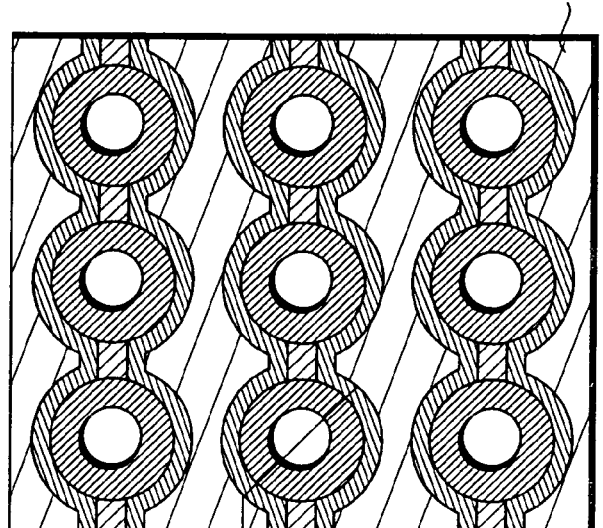

FIGS. 8A to 8D show an electrooptic system array having still another structure. FIG. 8A is an exploded sectional view of the electrooptic system array, FIG. 8B is a plan view of a middle electrode 2 when viewed from the top, FIG. 8C is a sectional view of the middle electrode 2, and FIG. 8D is a perspective view of a lower electrode 3, lower shield 5, upper electrode 1, and upper shield 4. Middle shield electrodes 16 are arranged between a plurality of cylindrical electrode elements of the middle electrode 2. This reduces the influence of an adjacent electric field in the cylindrical electrode elements of the middle electrode 2, and improves the anti-crosstalk effect.

FIGS. 9A to 9C show an electrooptic system array having still another structure. A middle electrode 2 comprises a plurality of rectangular electrode elements 2A, 2B, and 2C arrayed in units of rows, which enables applying different potentials to the respective arrays. These rectangular electrode elements increase the rigidity of the structure and also increase the process precision.

Figure 11A:
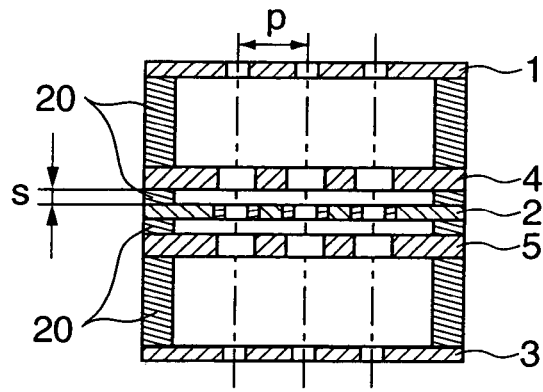
FIGS. 11A to 11E are views for explaining still another structure of an electrooptic system array.
Figure 11B:
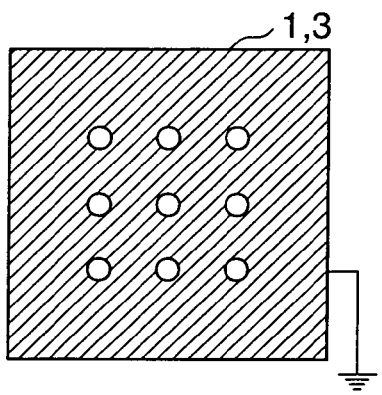
Figure 11C:
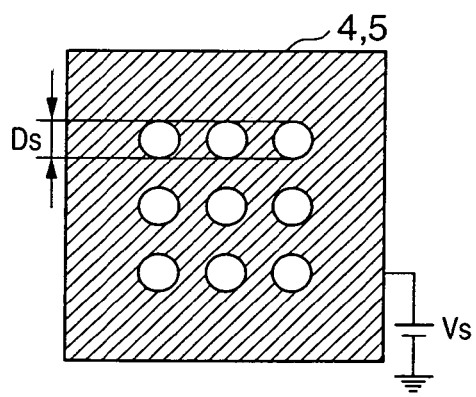
Figure 11D:
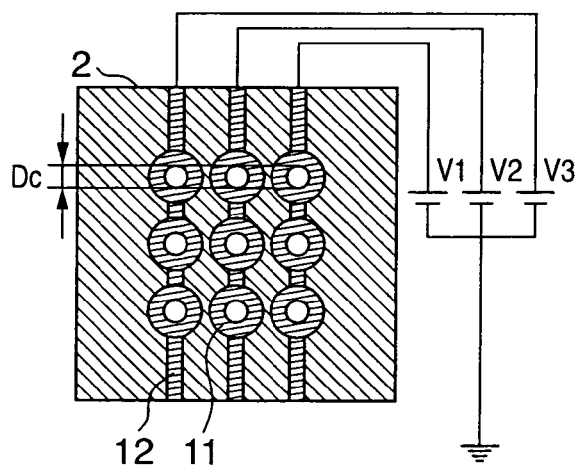

FIGS. 11A to 11E are views showing an electrooptic system array according to still another embodiment. FIG. 11A is a sectional view of the electrooptic system array, which has an upper, a middle and lower electrodes 1, 2, and 3, each having a plurality of aperture electrodes. Upper and lower shield electrodes 4 and 5 set to a common potential are arranged to sandwich the aperture electrodes (electrode elements) of the middle electrode 2. The aperture electrodes of the upper and lower shield electrodes 4 and 5 are arranged on the electron beam path. The electrodes 1, 2, and 3 and the shields 4 and 5 are stacked and integrated via insulating spacers 20. FIG. 11B shows the structure of the upper or lower electrode 1 or 3 in which all the aperture electrodes are grounded to a potential of 0 [V]. FIG. 11C shows the structure of the upper or lower shield electrodes 4 or 5 in which a common potential Vs (e.g., −500 V) is applied to all the aperture electrodes. FIG. 11D shows the structure of the middle electrode 2 in which different potentials V1, V2, and V3 (e.g., V1=−900 V, V2=−950 V, and V3=−1,000 V) are applied in units of rows of the aperture electrodes. Einzel lenses having middle electrodes on different rows exhibit different lens actions, and the middle electrodes can be regarded as setting electrodes for setting the lens actions of the Einzel lenses. The potentials may be applied in this manner not only in this arrangement but also in the other arrangements described above.

To effectively reduce crosstalk, intervals s between the middle electrode 2 and the upper and lower shield electrodes 4 and 5 are set smaller than a layout interval (pitch) p between aperture electrodes formed in the middle electrode 2, as shown in FIG. 11A. To reduce the influence of inserting the shield electrode on lens action, an aperture size Ds (inner diameter) of each electrode in the shield electrode 4 or 5 (see FIG. 11C) is set larger than an aperture size Dc (inner diameter) of each electrode in the middle electrode 2 (see FIG. 11D). The aperture size of each electrode of the shield electrode 4 or 5 is set larger than the aperture size of each electrode of the upper or lower electrode 1 or 3.

Figure 11E:
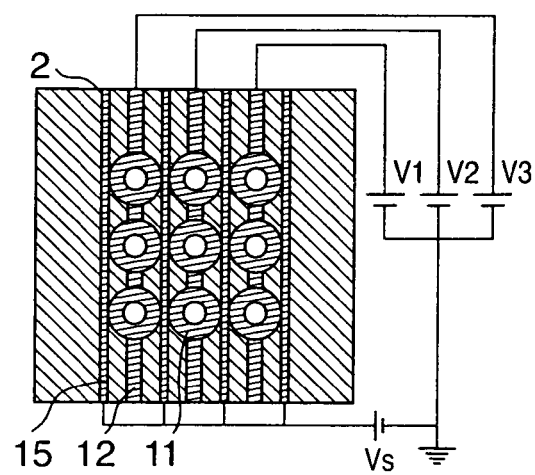

Instead of this structure, the middle electrode may be constituted as shown in FIG. 11E. In FIG. 11E, the middle electrode 2 comprises middle shield electrodes 15 linearly formed between the rows of electrode elements 11 set to different potentials (V1, V2, and V3). The middle shield electrodes 15 receive the same common potential Vs as the shield electrodes 4 and 5. Crosstalk is effectively prevented by shielding the electrode rows from each other within the middle electrode.

Figure 12A:
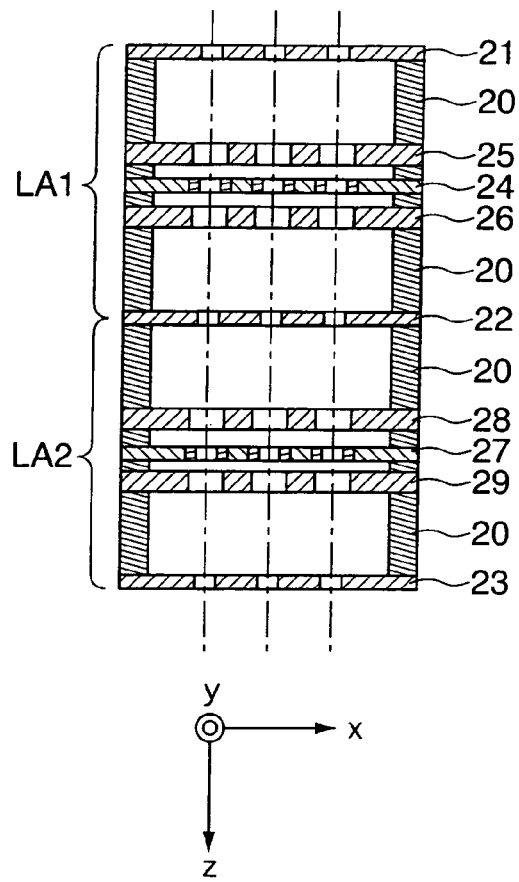
FIGS. 12A and 12B are views for explaining still another structure of an electrooptic system array.
Figure 12B:
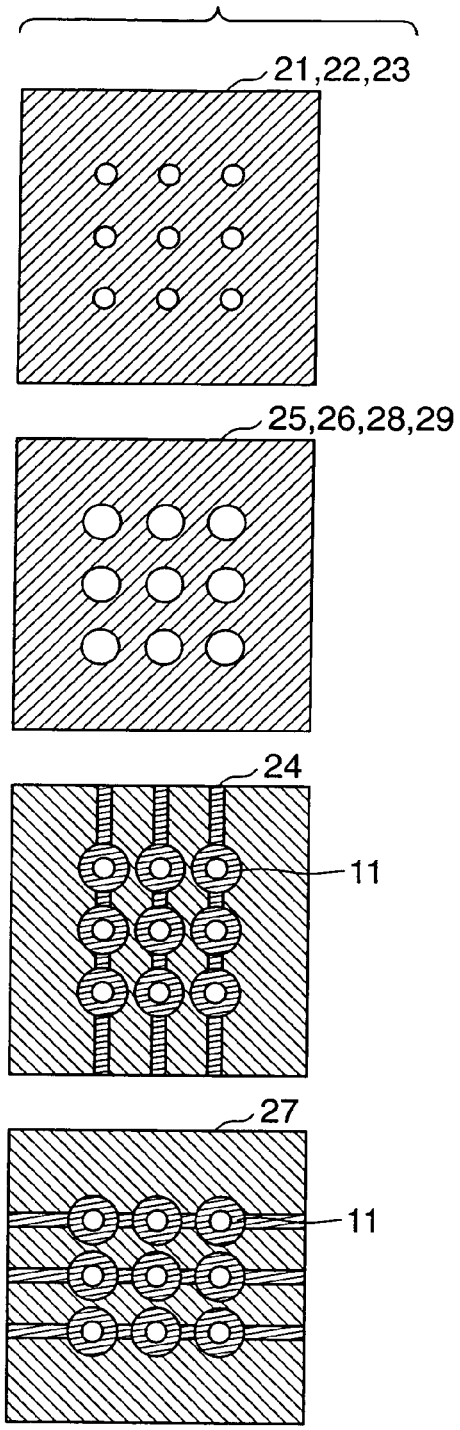

FIGS. 12A and 12B show still another modification. This modification adopts an integrated structure of a unit LA1 including a middle electrode 24 on which rows of electrode elements 11 are formed in the Y direction, and a unit LA2 including a middle electrode 27 on which rows of electrode elements 11 are formed in the perpendicular X direction. One electrode 22 serves as both the lower electrode of the unit LA1 and the upper electrode of the unit LA2. An upper electrode 21, the electrode 22, and a lower electrode 23 are grounded, and a total of four shield electrodes 25, 26, 28, and 29 receive the same potential Vs.

<Electron Beam Exposure Apparatus>

Figure 13:
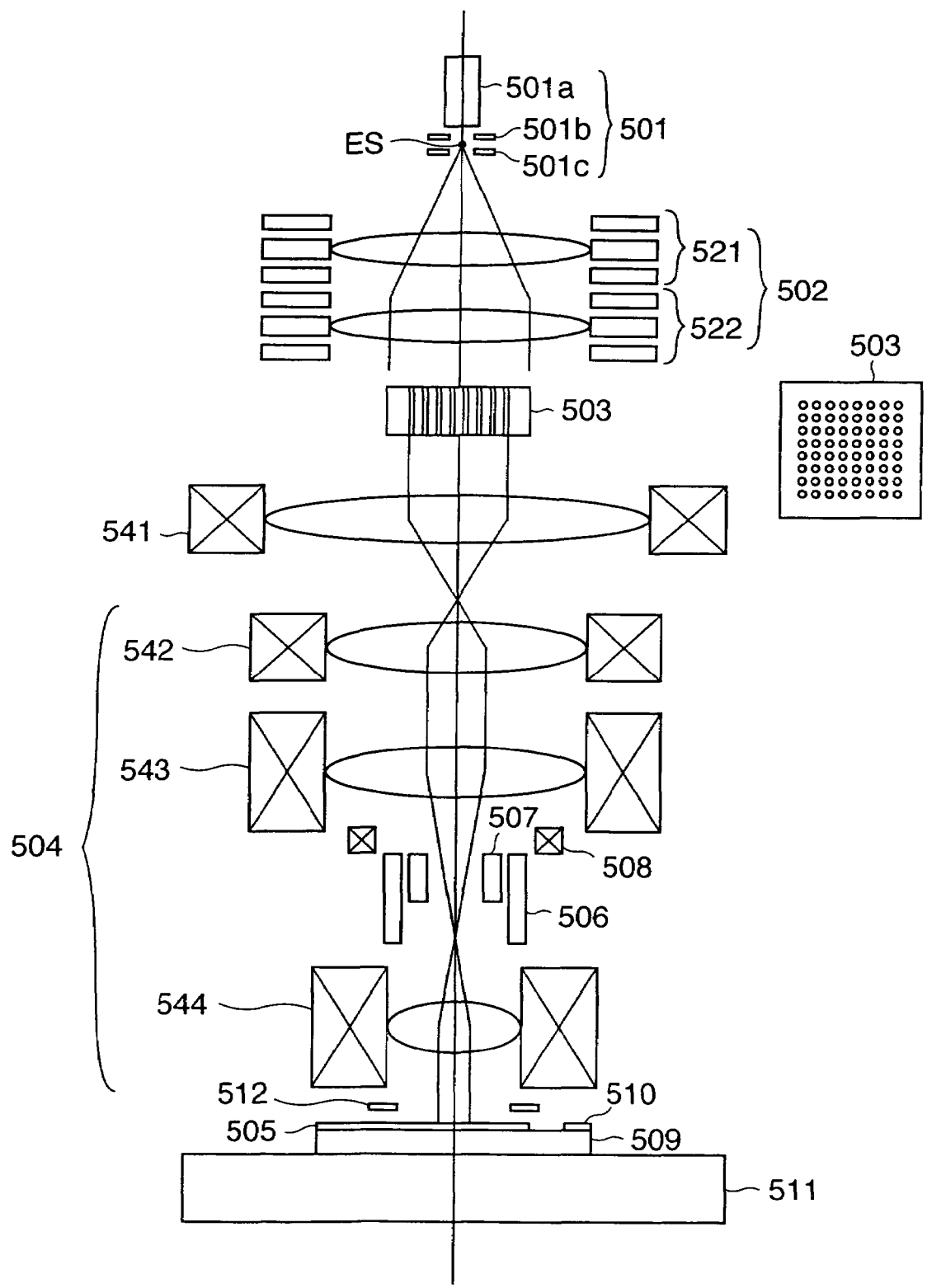
FIG. 13 is a view showing an entire multi-beam exposure apparatus.

A multi-beam charged-particle exposure apparatus (electron beam exposure apparatus) will be exemplified as a system using an electrooptic system array as described in the various embodiments. FIG. 13 is a schematic view showing the overall system. In FIG. 13, an electron gun 501 as a charged-particle source is constituted by a cathode 501a, grid 501b, and anode 501c. Electrons emitted by the cathode 501a form a crossover image (to be referred to as an electron source ES hereinafter) between the grid 501b and the anode 501c. An electron beam emitted by the electron source ES irradiates a correction electrooptic system 503 via an irradiation electrooptic system 502 serving as a condenser lens. The irradiation electrooptic system 502 is comprised of electron lenses (Einzel lenses) 521 and 522 each having three separate electrodes. The correction electrooptic system 503 includes an electrooptic system array to which the electrooptic system arrays are applied, and forms a plurality of intermediate images of the electron source ES (details of the structure will be described later). The correction electrooptic system 503 adjusts the formation positions of intermediate images so as to correct the influence of aberration of a projection electrooptic system 504. Each intermediate image formed by the correction electrooptic system 503 is reduced and projected by the projection electrooptic system 504, and forms an image of the electron source ES on a wafer 505 as a surface to be exposed. The projection electrooptic system 504 is constituted by a symmetrical magnet doublet made up of a first projection lens 541 (543) and second projection lens 542 (544). Reference numeral 506 denotes a deflector for deflecting a plurality of electron beams from the correction electrooptic system 503 and simultaneously displacing a plurality of electron source images on the wafer 505 in the X and Y directions; 507, a dynamic focus coil for correcting a shift in the focal position of a light source image caused by deflection aberration generated when the deflector 506 operates; 508, a dynamic stigmatic coil for correcting astigmatism among deflection aberrations generated by deflection; 509, a θ-Z stage which supports the wafer 505, is movable in the optical axis AX (Z-axis) direction and the rotational direction around the Z-axis, and has a stage reference plate 510 fixed thereto; 511, an X-Y stage which supports the θ-Z stage and is movable in the X and Y directions perpendicular to the optical axis AX (Z-axis); and 512, a reflected-electron detector for detecting reflected electrons generated upon irradiating a mark on the stage reference plate 510 with an electron beam.

Figure 14A:
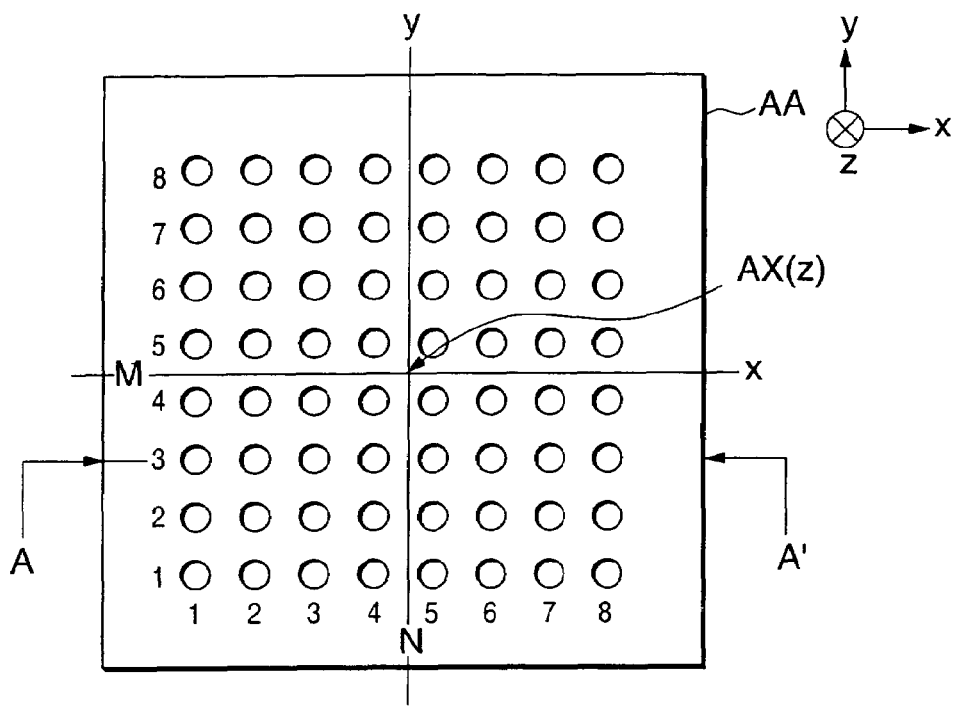
FIGS. 14A and 14B are views for explaining details of a correction electrooptic system.
Figure 14B:
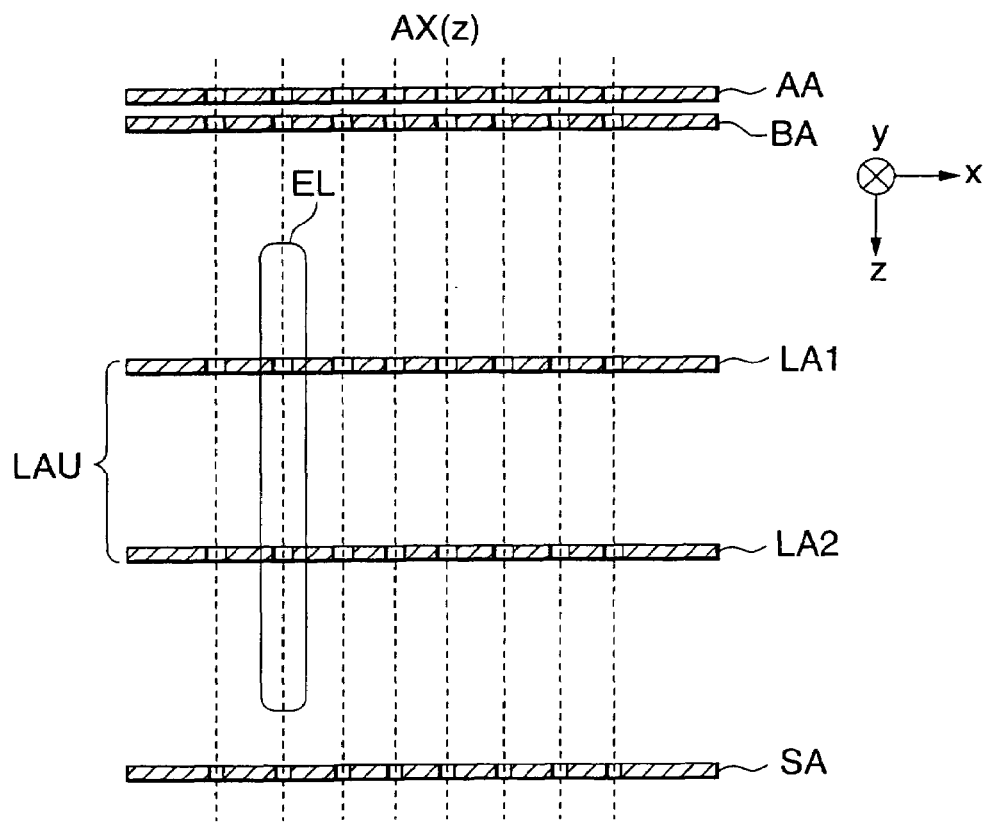

FIGS. 14A and 14B are views for explaining details of the correction electrooptic system 503. The correction electrooptic system 503 comprises an aperture array AA, blanker array BA, element electrooptic system array unit LAU, and stopper array SA along the optical axis. FIG. 14A is a view of the correction electrooptic system 503 when viewed from the electron gun 501, and FIG. 14B is a section view taken along the line A–A' in FIG. 14A. As shown in FIG. 14A, the aperture array AA has an array (8×8) of apertures regularly formed in a substrate, and splits an incident electron beam into a plurality of (64) electron beams. The blanker array BA is constituted by forming on one substrate a plurality of deflectors for individually deflecting a plurality of electron beams split by the aperture array AA. The element electrooptic system array unit LAU is formed from first and second electrooptic system arrays LA1 and LA2 as electron lens arrays each prepared by two-dimensionally arraying a plurality of electron lenses on the same plane. The electrooptic system arrays LA1 and LA2 have a structure as an application of the electrooptic system arrays described in the above embodiments to an 8×8 array. The first and second electrooptic system arrays LA1 and LA2 are fabricated by the above-mentioned method. The element electrooptic system array unit LAU constitutes one element electrooptic system EL by the electron lenses of the first and second electrooptic system arrays LA1 and LA2 that use the common X-Y coordinate system. The stopper array SA has a plurality of apertures formed in a substrate, similar to the aperture array AA. Only a beam deflected by the blanker array BA is shielded by the stopper array SA, and ON/OFF operation of an incident beam to the wafer 505 is switched for each beam under the control of the blanker array.

Since the charged-particle beam exposure apparatus of this embodiment adopts an excellent electrooptic system array as described above for the correction electrooptic system, an apparatus having a very high exposure precision can be provided and can increase the integration degree of a device to be manufactured in comparison with the prior art.

<Example of Semiconductor Production System>

A production system for producing a semiconductor device (e.g., a semiconductor chip such as an IC or LSI, a liquid crystal panel, a CCD, a thin-film magnetic head, a micromachine, or the like) using the exposure apparatus will be exemplified. A trouble remedy or periodic maintenance of a manufacturing apparatus installed in a semiconductor manufacturing factory, or maintenance service such as software distribution is performed by using a computer network outside the manufacturing factory.

Figure 15:
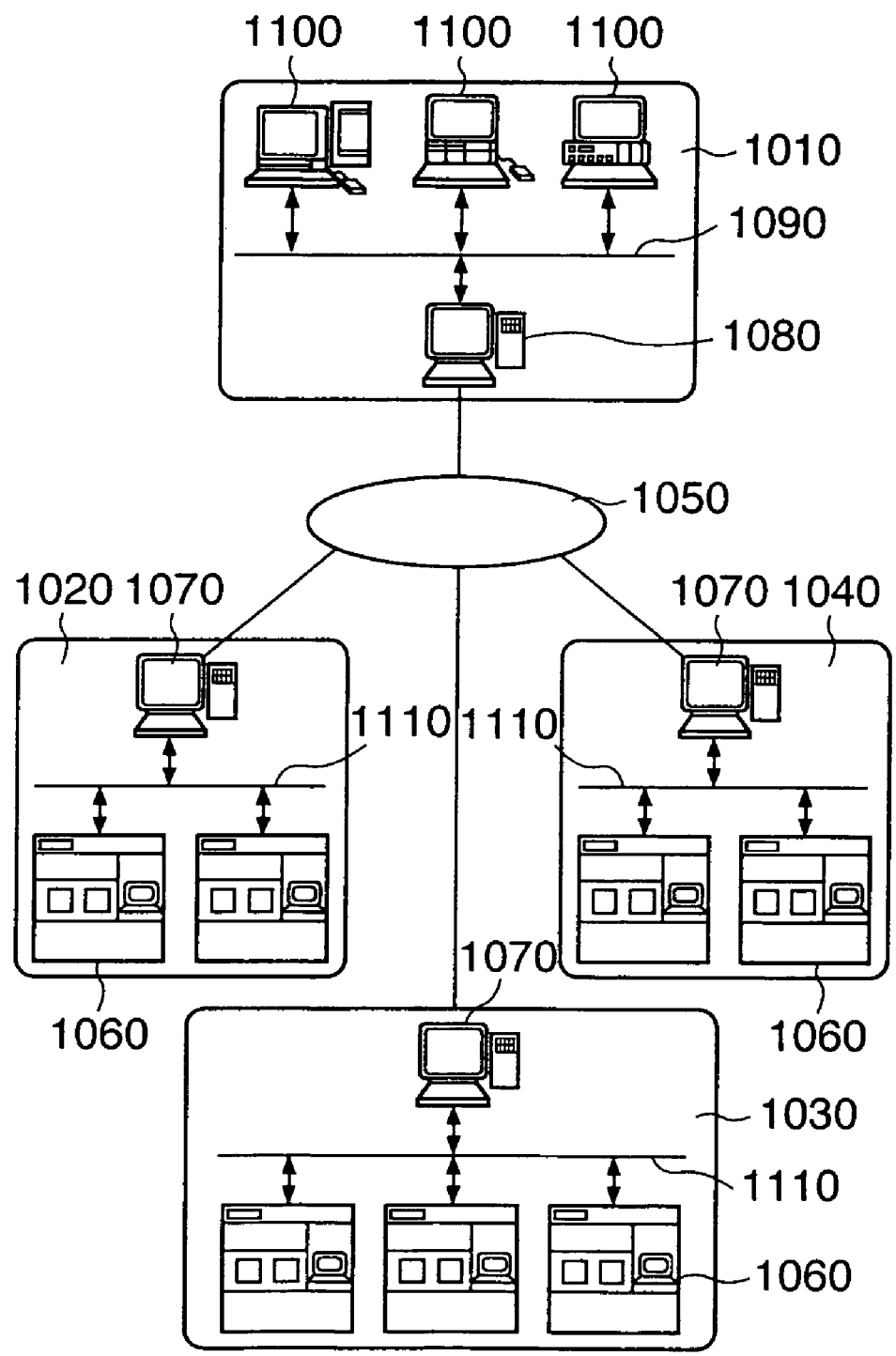
FIG. 15 is a view showing the concept of a semiconductor device production system when viewed from a given angle.

FIG. 15 shows the overall system cut out at a given angle. In FIG. 15, reference numeral 1010 denotes a business office of a vendor (e.g., an apparatus supply manufacturer), which provides a semiconductor device manufacturing apparatus. Assumed examples of the manufacturing apparatus are semiconductor manufacturing apparatuses for performing various processes used in a semiconductor manufacturing factory, such as pre-process apparatuses (e.g., a lithography apparatus including an exposure apparatus, a resist processing apparatus and an etching apparatus, an annealing apparatus, a film formation apparatus, a planarization apparatus, and the like) and post-process apparatuses (e.g., an assembly apparatus, an inspection apparatus, and the like). The business office 1010 comprises a host management system 1080 for providing a maintenance database for the manufacturing apparatus, a plurality of operation terminal computers 1100, and a LAN (Local Area Network) 1090, which connects the host management system 1080 and computers 1100 to construct an intranet. The host management system 1080 has a gateway for connecting the LAN 1090 to Internet 1050 as an external network of the business office, and a security function for limiting external access.

Reference numerals 1020 to 1040 denote manufacturing factories of the semiconductor manufacturer as users of manufacturing apparatuses. The manufacturing factories 1020 to 1040 may belong to different manufacturers or the same manufacturer (e.g., a pre-process factory, a post-process factory, and the like). Each of the factories 1020 to 1040 is equipped with a plurality of manufacturing apparatuses 1060, a LAN (Local Area Network) 1110, which connects these apparatuses 1060 to construct an intranet, and a host management system 1070 serving as a monitoring apparatus for monitoring the operation status of each manufacturing apparatus 1060. The host management system 1070 in each of the factories 1020 to 1040 has a gateway for connecting the LAN 1110 in the factory to the Internet 1050 as an external network of the factory. Each factory can access the host management system 1080 of the vendor 1010 from the LAN 1110 via the Internet 1050. Typically, the security function of the host management system 1080 authorizes access of only a limited user to the host management system 1080.

In this system, the factory notifies the vendor via the Internet 1050 of status information (e.g., the symptom of a manufacturing apparatus in trouble) representing the operation status of each manufacturing apparatus 1060. The vendor transmits, to the factory, response information (e.g., information designating a remedy against the trouble, or remedy software or data) corresponding to the notification, or maintenance information such as the latest software or help information. Data communication between the factories 1020 to 1040 and the vendor 1010 and data communication via the LAN 1110 in each factory typically adopt a communication protocol (TCP/IP) generally used in the Internet. Instead of using the Internet as an external network of the factory, a dedicated-line network (e.g., an ISDN) having high security, which inhibits access of a third party, can be adopted. It is also possible that the user constructs a database in addition to one provided by the vendor and sets the database on an external network and that the host management system authorizes access to the database from a plurality of user factories.

Figure 16:
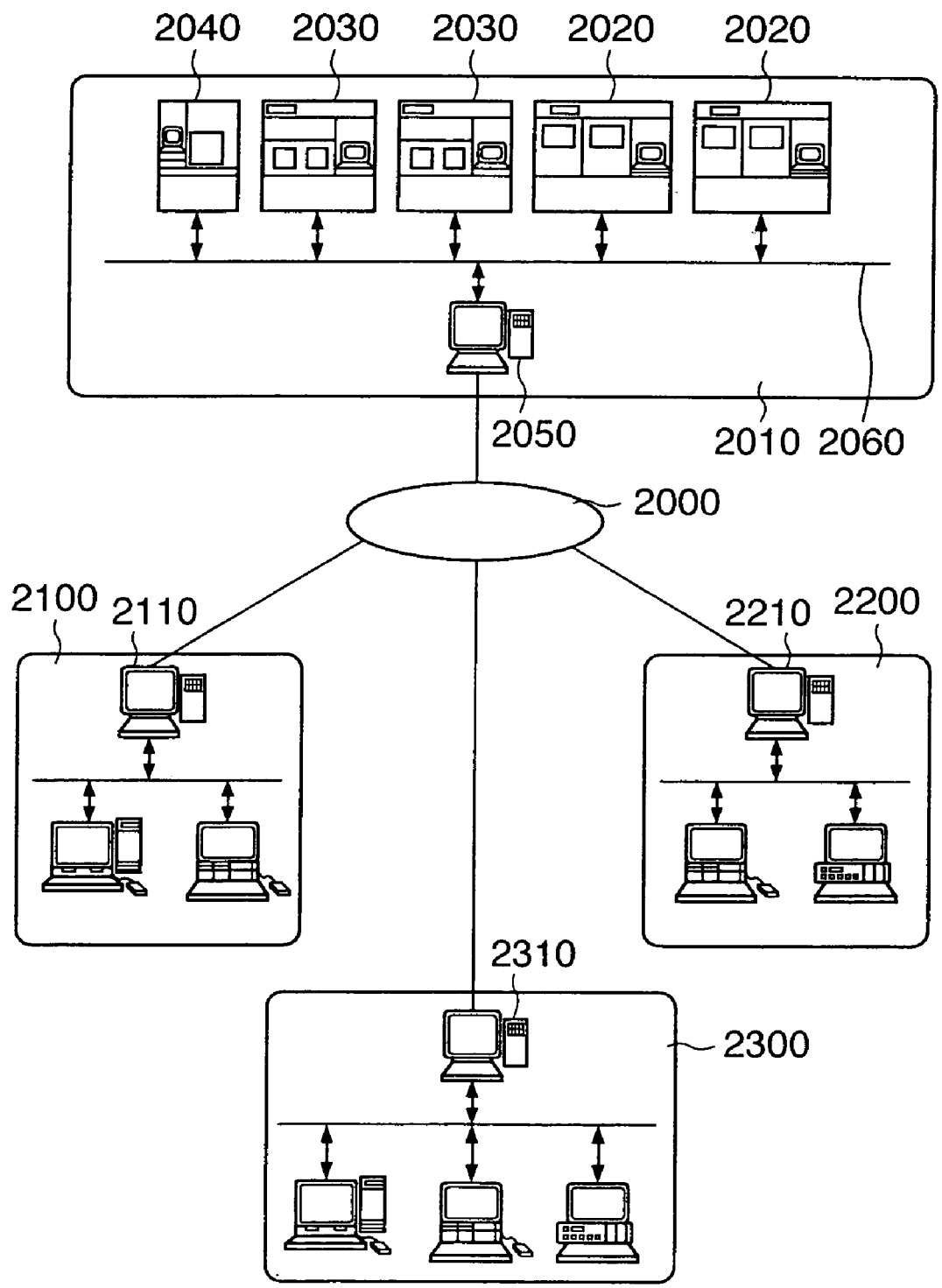
FIG. 16 is a view showing the concept of the semiconductor device production system when viewed from another angle.

FIG. 16 is a view showing the concept of the overall system of this embodiment that is cut out at a different angle from FIG. 15. In the above example, a plurality of user factories having manufacturing apparatuses and the management system of the manufacturing apparatus vendor are connected via an external network, and production management of each factory or information of at least one manufacturing apparatus is communicated via the external network. In the example of FIG. 16, a factory having a plurality of manufacturing apparatuses of a plurality of vendors, and the management systems of the vendors for these manufacturing apparatuses are connected via the external network of the factory, and maintenance information of each manufacturing factory is communicated. In FIG. 16, reference numeral 2010 denotes a manufacturing factory of a manufacturing apparatus user (e.g., a semiconductor device manufacturer) where manufacturing apparatuses for performing various processes, e.g., an exposure apparatus 2020, a resist processing apparatus 2030, and a film formation apparatus 2040 are installed in the manufacturing line of the factory. FIG. 16 shows only one manufacturing factory 2010, but a plurality of factories are networked in practice. The respective apparatuses in the factory are connected to a LAN 2060 to construct an intranet, and a host management system 2050 manages the operation of the manufacturing line. The business offices of vendors (e.g., apparatus supply manufacturers) such as an exposure apparatus manufacturer 2100, a resist processing apparatus manufacturer 2200, and a film formation apparatus manufacturer 2300 comprise host management systems 2110, 2210, 2310 for executing remote maintenance for the supplied apparatuses. Each host management system has a maintenance database and a gateway for an external network, as described above. The host management system 2050 for managing the apparatuses in the manufacturing factory of the user, and the management systems 2110, 2210, and 2310 of the vendors for the respective apparatuses are connected via the Internet or dedicated-line network serving as an external network 2000. If trouble occurs in any one of a series of manufacturing apparatuses along the manufacturing line in this system, the operation of the manufacturing line stops. This trouble can be quickly solved by remote maintenance from the vendor of the apparatus in trouble via the external network 2000. This can minimize the stoppage of the manufacturing line.

Each manufacturing apparatus in the semiconductor manufacturing factory comprises a display, a network interface, and a computer for executing network access software and apparatus operating software, which are stored in a storage device. The storage device is a built-in memory, a hard disk, or a network file server. The network access software includes a dedicated or general-purpose web browser, and provides a user interface having a window as shown in FIG. 17 on the display. While referring to this window, the operator who manages manufacturing apparatuses in each factory inputs, in input items on the windows, pieces of information such as the type of manufacturing apparatus (4010), serial number (4020), subject of trouble (4030), occurrence date (4040), degree of urgency (4050), symptom (4060), remedy (4070), and progress (4080). The pieces of input information are transmitted to the maintenance database via the Internet, and appropriate maintenance information is sent back from the maintenance database and displayed on the display. The user interface provided by the web browser realizes hyperlink functions (4100 to 4120), as shown in FIG. 17. This allows the operator to access detailed information of each item, to receive the latest-version software to be used for a manufacturing apparatus from a software library provided by a vendor, and to receive an operation guide (help information) as a reference for the operator in the factory.

Figure 18:
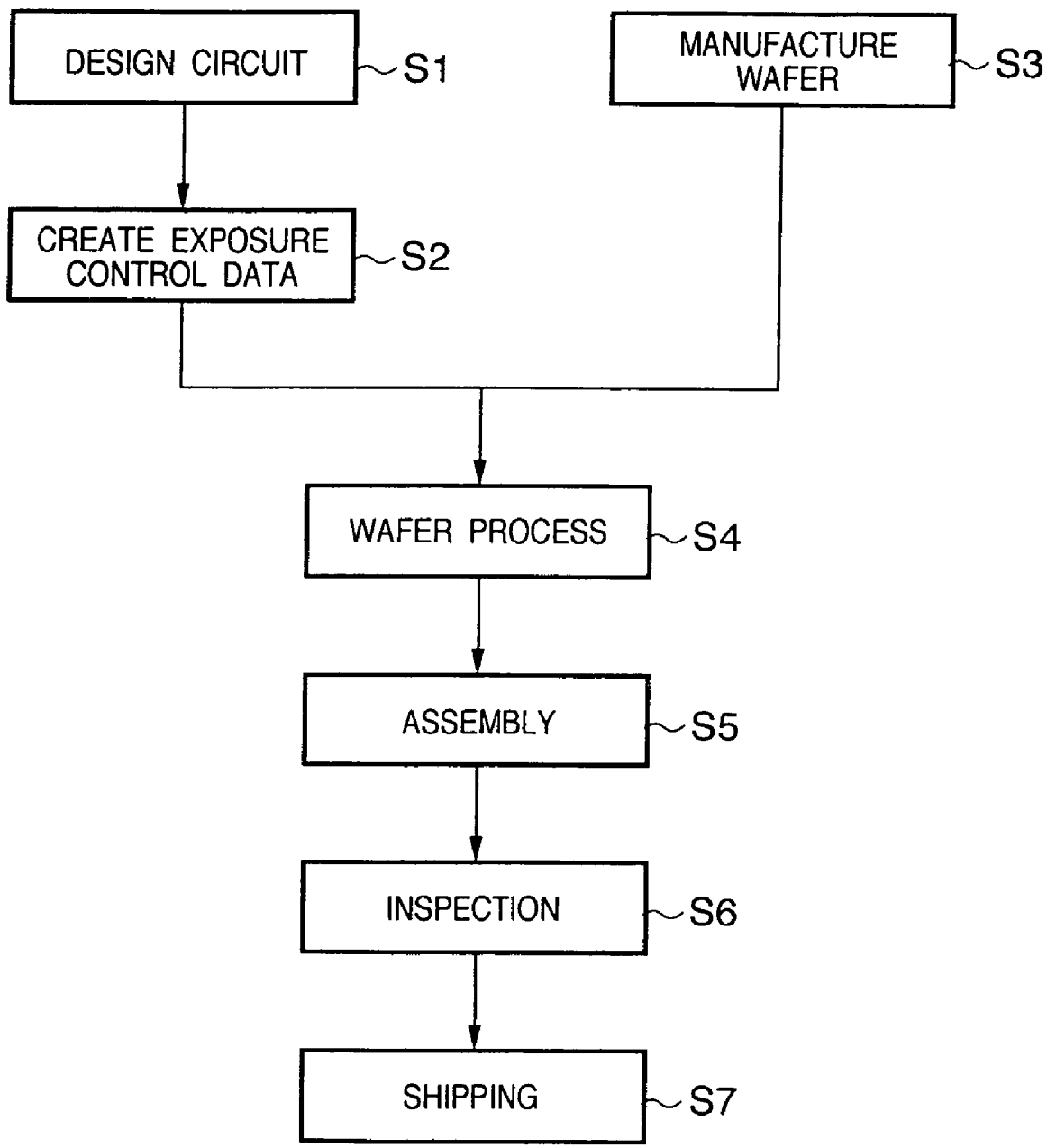
FIG. 18 is a flow chart for explaining the flow of a semiconductor device manufacturing process.

A semiconductor device manufacturing process using the above-described production system will be explained. FIG. 18 shows the flow of the whole manufacturing process of the semiconductor device. In step 1 (circuit design), a semiconductor device circuit is designed. In step 2 (creation of exposure control data), exposure control data of the exposure apparatus is created based on the designed circuit pattern. In step 3 (wafer manufacture), a wafer is manufactured using a material such as silicon. In step 4 (wafer process), called a pre-process, an actual circuit is formed on the wafer by lithography using a prepared mask and wafer. Step 5 (assembly), called a post-process, is the step of forming a semiconductor chip by using the wafer manufactured in step 4, and includes an assembly process (dicing and bonding) and a packaging process (chip encapsulation). In step 6 (inspection), inspections such as the operation confirmation test and durability test of the semiconductor device manufactured in step 5 are conducted. After these steps, the semiconductor device is completed and shipped (step 7). For example, the pre-process and post-process may be performed in separate dedicated factories. In this case, maintenance is done for each of the factories by the above-described remote maintenance system. Information for production management and apparatus maintenance is communicated between the pre-process factory and the post-process factory via the Internet or dedicated-line network.

Figure 19:
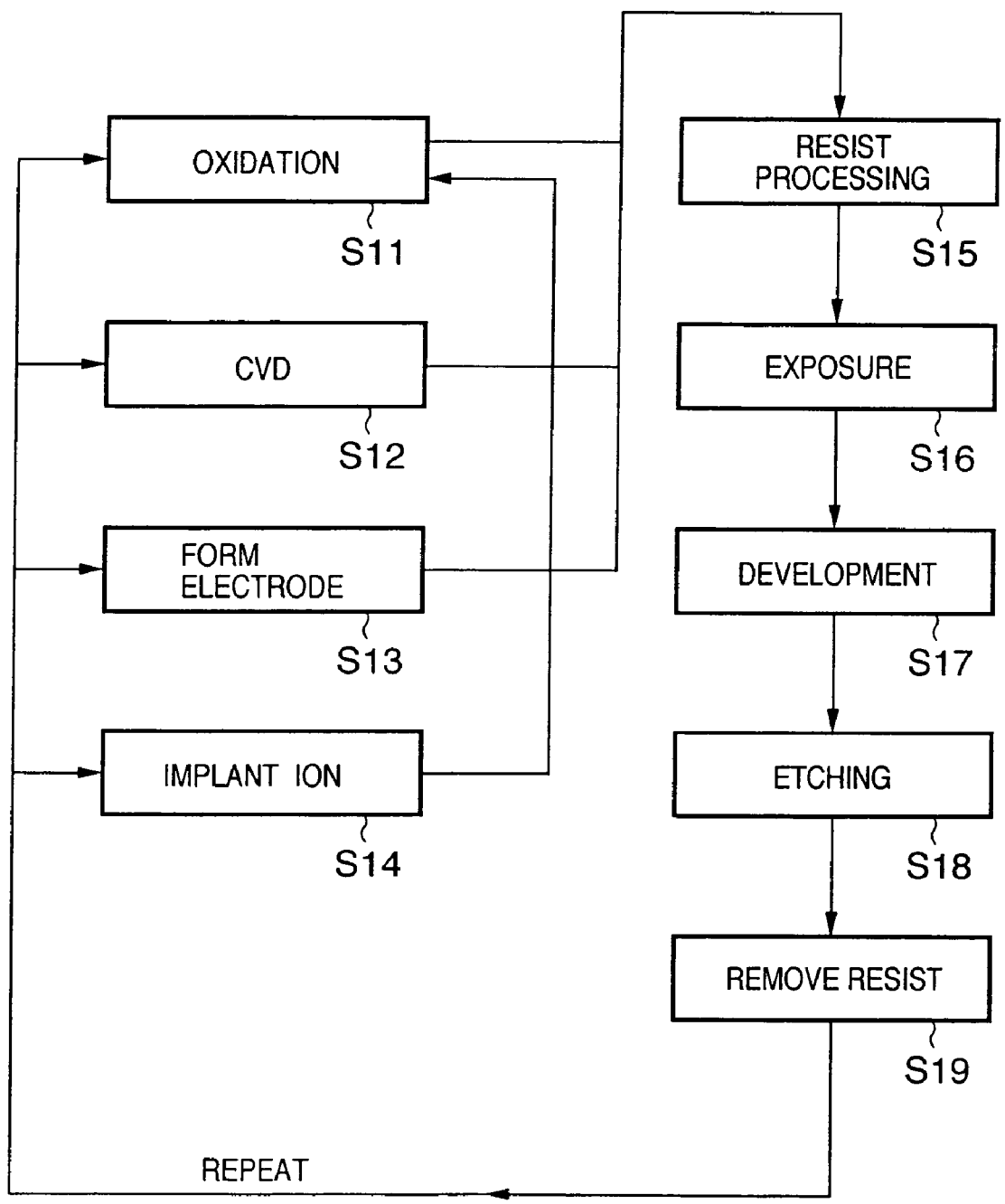
FIG. 19 is a flow chart for explaining details of a wafer process.

FIG. 19 shows the detailed flow of the wafer process. In step 11 (oxidation), the wafer surface is oxidized. In step 12 (CVD), an insulating film is formed on the wafer surface. In step 13 (electrode formation), an electrode is formed on the wafer by vapor deposition. In step 14 (ion implantation), ions are implanted in the wafer. In step 15 (resist processing), a photosensitive agent is applied to the wafer. In step 16 (exposure), the above-mentioned exposure apparatus draws (exposes) a circuit pattern on the wafer. In step 17 (developing), the exposed wafer is developed. In step 18 (etching), the resist is etched except for the developed resist image. In step 19 (resist removal), an unnecessary resist after etching is removed. These steps are repeated to form multiple circuit patterns on the wafer. A manufacturing apparatus used in each step undergoes maintenance by the remote maintenance system, which prevents trouble in advance. Even if trouble occurs, the manufacturing apparatus can be quickly recovered. The productivity of the semiconductor device can be increased in comparison with the prior art.

The present invention can provide, e.g., an electrooptic system array which solves crosstalk unique to a multi-beam and realizes various conditions such as downsizing, high precision, and high reliability at a high level. The present invention can also provide a high-precision exposure apparatus using the electrooptic system array, a high-productivity device manufacturing method, a semiconductor device production factory, and the like.

As many apparently widely different embodiments of the present invention can be made without departing from the spirit and scope thereof, it is to be understood that the invention is not limited to the specific embodiments thereof except as defined in the appended claims.

What is claimed is:

1. A charged-particle beam exposure apparatus comprising:

a charged-particle beam source for emitting a charged-particle beam;

an electrooptic system array which has a plurality of electron lenses and forms a plurality of intermediate images of said charged-particle beam source by the plurality of electron lenses; and a projection electrooptic system for projecting on a substrate the plurality of intermediate images formed by said electrooptic system array, said electrooptic system array including:

at least two electrodes arranged along paths of a plurality of charged-particle beams, each of said at least two electrodes having a plurality of apertures on the paths of the plurality of charged-particle beams; and a shield electrode which is interposed between said at least two electrodes and has a plurality of shields corresponding to the respective paths of the plurality of charged-particle beams.

2. A charged-particle beam exposure apparatus comprising:

a charged-particle beam source for emitting a charged-particle beam;

an electrooptic system array which has a plurality of electron lenses and forms a plurality of intermediate images of said charged-particle beam source by the plurality of electron lenses; and a projection electrooptic system for projecting on a substrate the plurality of intermediate images formed by said electrooptic system array, said electrooptic system array including:

upper, middle, and lower electrodes arranged along paths of a plurality of charged-particle beams, said upper, middle, and lower electrodes having pluralities of apertures on the paths of the plurality of charged-particle beams; and a lower shield electrode which is interposed between said lower and middle electrodes and has a plurality of shields corresponding to the respective paths of the plurality of charged-particle beams.

3. A device manufacturing method comprising the steps of:

installing a plurality of semiconductor manufacturing apparatuses including a charged-particle beam exposure apparatus in a factory; and manufacturing a semiconductor device by using the plurality of semiconductor manufacturing apparatuses, the charged-particle beam exposure apparatus having:

a charged-particle beam source for emitting a charged-particle beam;

an electrooptic system array which has a plurality of electron lenses and forms a plurality of intermediate images of the charged-particle beam source by the plurality of electron lenses; and a projection electrooptic system for projecting on a substrate the plurality of intermediate images formed by the electrooptic system array, the electrooptic system array including:

at least two electrodes arranged along paths of a plurality of charged-particle beams, each of the at least two electrodes having a plurality of apertures on the paths of the plurality of charged-particle beams; and a shield electrode which is interposed between the at least two electrodes and has a plurality of shields corresponding to the respective paths of the plurality of charged-particle beams.

4. The method according to claim 3, further comprising the steps of:

connecting the plurality of semiconductor manufacturing apparatuses by a local area network;

connecting the local area network to an external network of the factory;

acquiring information about the charged-particle beam exposure apparatus from a database on the external network by using the local area network and the external network; and controlling the charged-particle beam exposure apparatus on the basis of the acquired information.

* * * * *

UNITED STATES PATENT AND TRADEMARK OFFICE
CERTIFICATE OF CORRECTION

| | | |
|---|---|---|
| PATENT NO. | : 7,126,141 B2 | Page 1 of 1 |
| APPLICATION NO. | : 11/168425 | |
| DATED | : October 24, 2006 | |
| INVENTOR(S) | : Haruhito Ono et al. | |

It is certified that error appears in the above-identified patent and that said Letters Patent is hereby corrected as shown below:

IN THE DRAWINGS:
"Sheet 10 of 19," "FIG. 10" should be deleted and replaced with the following.

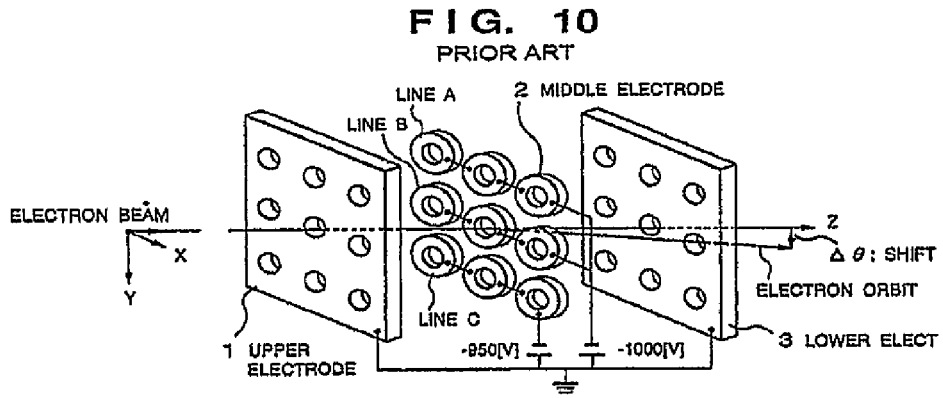

COLUMN 3:
Line 62, "prefer-red" should read -- preferred --.

Signed and Sealed this

Eleventh Day of September, 2007

JON W. DUDAS
*Director of the United States Patent and Trademark Office*